(12) United States Patent
Preishuber-Pflügl et al.

(10) Patent No.: US 7,268,095 B2
(45) Date of Patent: Sep. 11, 2007

(54) TRANSITION METAL CATALYSTS FOR (CO) POLYMERIZING OF OLEFINIC MONOMERS

(75) Inventors: Peter Preishuber-Pflügl, Ludwigshafen (DE); Jun Okuda, Ingelheim (DE); Valentine Reimer, Wiesbaden (DE); Marc Oliver Kristen, Kelkheim (DE)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 10/533,945

(22) PCT Filed: Nov. 3, 2003

(86) PCT No.: PCT/EP03/12200

§ 371 (c)(1),
(2), (4) Date: May 4, 2005

(87) PCT Pub. No.: WO2004/041796

PCT Pub. Date: May 21, 2004

(65) Prior Publication Data

US 2006/0128559 A1    Jun. 15, 2006

(30) Foreign Application Priority Data

Nov. 4, 2002  (DE) .............. 102 51 513

(51) Int. Cl.
C08F 4/02 (2006.01)
C08F 4/44 (2006.01)
B01J 31/00 (2006.01)
C07F 9/02 (2006.01)
C07F 9/30 (2006.01)
C07F 17/00 (2006.01)
C07D 277/00 (2006.01)

(52) U.S. Cl. .............. 502/117; 502/103; 502/167; 502/168; 502/169; 556/19; 556/50; 556/43; 548/190; 548/199; 548/202; 548/403; 526/161; 526/165

(58) Field of Classification Search .......... 526/161, 526/165; 502/103, 117, 167–169, 171; 556/19, 556/20, 43; 548/190, 199, 202, 403, 564, 548/565, 579

See application file for complete search history.

(56) References Cited

U.S. PATENT DOCUMENTS 3,673,152 A * 6/1972 Minagawa et al. .......... 524/83
4,990,640 A    2/1991 Tsutsui et al.
5,155,080 A   10/1992 Elder et al.
5,225,500 A    7/1993 Elder et al.
5,321,106 A    6/1994 LaPointe
6,309,997 B1  10/2001 Fujita et al.

(Continued)

FOREIGN PATENT DOCUMENTS

EP    0 283 390    * 9/1988

(Continued)

OTHER PUBLICATIONS

Richard F. Jordan et al., Organometallics 1997, vol. 16, No. 15 3282 to 3302, (1997).

(Continued)

*Primary Examiner*—Aileen Felton
*Assistant Examiner*—J. Eric McDonough

(57) ABSTRACT

A compound of the formula Ia or Ib;

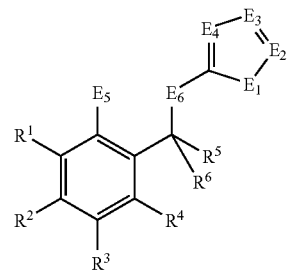

Ia

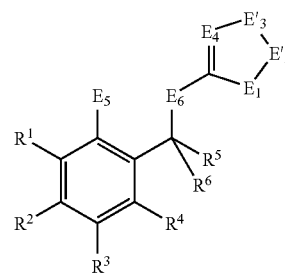

Ib where,
in the formula Ia,
$E_1$ is O, S, Se, Te, NR, $CR_2$, or PR;
$E_2$, $E_3$ are each CR, N, or P;
$E_4$ is N, or P;
$E_5$ is OH, SH, NHR, OR', SR', or NRR';
$E_6$ is NH, PH, NR', or PR';
$R^5$, $R^6$ are each hydrogen or a linear, branched or cyclic alkyl radical or an aryl radical;
$R^1$, $R^2$, $R^3$, $R^4$ are each hydrogen, a linear, branched or cyclic alkyl radical, an aryl radical, a halogen or a nitro group;
R is hydrogen, a linear, branched or cyclic alkyl radical;
R' is a linear, branched or cyclic alkyl radical;
where at least one of the groups $E_5$ and $E_6$ contains a hydrogen atom; and in the formula Ib,
the symbols $E_1$, $E_4$, $E_5$, $E_6$, $R^5$, $R^6$, $R^1$, $R^2$, $R^3$, $R^4$, R and R' are as defined in formula Ia;
and
$E'_2$ and $E'_3$ are each O, S, Se, Te, NR, $CR_2$, or PR.

16 Claims, No Drawings

U.S. PATENT DOCUMENTS

| | | |
|---|---|---|
| 6,559,091 B1 | 5/2003 | Moody et al. |
| 6,593,266 B1 | 7/2003 | Matsui et al. |
| 2002/0055600 A1 | 5/2002 | Fujita et al. |
| 2002/0115557 A1 | 8/2002 | Fujita et al. |
| 2003/0158199 A1* | 8/2003 | Stieber et al. ............... 514/242 |
| 2003/0195110 A1 | 10/2003 | Moody et al. |
| 2003/0225228 A1 | 12/2003 | Moody et al. |
| 2004/0102493 A1* | 5/2004 | Beswick et al. ............ 514/365 |
| 2004/0192743 A1* | 9/2004 | Mjalli et al. ................. 514/365 |

FOREIGN PATENT DOCUMENTS

| | | |
|---|---|---|
| EP | 0 426 637 B1 | 5/1991 |
| EP | 0 426 638 B1 | 5/1991 |
| EP | 427 697 | 5/1991 |
| EP | 0 874 005 A1 | 10/1998 |
| EP | 0 950 667 A2 | 10/1999 |
| EP | 1 174 442 A1 | 1/2002 |
| JP | 20786870 | 3/1990 |
| JP | 3179005 | 8/1991 |
| JP | 3179006 | 8/1991 |
| WO | WO88/05792 | 8/1988 |
| WO | WO88/05793 | 8/1988 |
| WO | WO98/27124 | 6/1998 |
| WO | WO 00/50470 | 8/2000 |

OTHER PUBLICATIONS

Synthesis and Structural Studies of Metal Complexes 505 (2002), Asian J. Chem vol. 14, No. 1, pp 503-505.

Studies on Co (II) and Ni (II) Complexes of Newly Synthesised Heterocyclic Schiff Bases (2002), J. Institute Chemists, vol. 74, part 6, pp. 188-190.

* cited by examiner

TRANSITION METAL CATALYSTS FOR (CO) POLYMERIZING OF OLEFINIC MONOMERS

This application is the U.S. national phase of International Application PCT/EP03/12200, filed Nov. 3, 2003.

The present invention relates to metal complexes which are composed of a transition metal and at least one polydentate ligand, to a process for preparing the metal complexes, to the polydentate ligands themselves and their preparation, to catalytically active compositions comprising the metal complex of the present invention, to the use of the catalytic composition of the present invention for the polymerization or copolymerization of olefins and to a process for the polymerization or copolymerization of olefins in which the catalytic composition of the present invention is used and to a polymer or a copolymer which can be prepared by the process of the present invention.

Polymers and copolymers of olefins are of great economic importance, since the monomers are readily available in large quantities and because the polymers can be varied within a wide range by varying the production process or the processing parameters. In the process for preparing the polymers or copolymers, the catalyst used is of particular importance. Apart from Ziegler-Natta catalysts, various single-site catalysts in which transition metals such as Zr (e.g. in metallocene catalysts), Ni, Pd or Fe or Co are used as central atoms are becoming increasingly important.

The thoroughly studied metallocene catalysts have disadvantages for industrial use. The most frequently used metallocenes are zirconocenes and hafnocenes which are very sensitive to hydrolysis. Furthermore, most metallocenes are sensitive to many catalyst poisons such as alcohols, ethers or carbon monoxide, which requires careful purification of the olefins used as monomers.

EP-A 0 874 005 relates to polymerization catalysts comprising transition metal compounds comprising one or more bidentate ligands. The transition metal complexes are preferably Ti complexes containing salicylaldimine. In these, the aldimine nitrogen may bear phenyl substituents or be incorporated in a six-membered ring. These catalysts generally produce low molecular weight polyethylenes which are not very suitable as materials.

EP-A 0 950 667 likewise relates to polymerization catalysts comprising transition metal compounds comprising one or more bidentate ligands. The coordination to the transition metal is via at least one nitrogen atom and at least one atom bound to an aromatic radical. Preferred transition metals are, according to the examples, titanium and zirconium.

Richard F. Jordan et al., Organometallics 1997, 16, 3282-3302, relates to transition metal complexes of group IV transition metals bearing bidentate 8-quinolinolato ligands. These metal complexes are used in ethylene polymerization. However, the activities of the complexes are very low.

WO 98/27124 relates to iron and cobalt complexes of 2,6-pyridine-carboxaldebis(imines) and 2,6-diacylpyridinebis(imines) which are used as catalysts for ethylene polymerization. These catalysts comprise tridentate ligands which are coordinated via three nitrogen atoms to the transition metal.

Owing to the great commercial importance of polyolefins, the search for very versatile polymerization of an active transition metal complex continues to be of great importance. It is of particular importance that the transition metal catalysts have not only a high activity but also a good stability. Many monodentate or bidentate ligands form active polymerization catalysts with various transition metal salts. However, these catalysts frequently display a decrease in the concentration of the active species during the course of the polymerization.

It is an object of the present invention to provide ligands, transition metal complexes containing these ligands and polymerization catalysts comprising these transition metal complexes which are stabilized and thus solve the problem of the decrease in the concentration of the active species during the course of the polymerization.

We have found that this object is achieved by a compound of the formula (Ia) or (Ib)

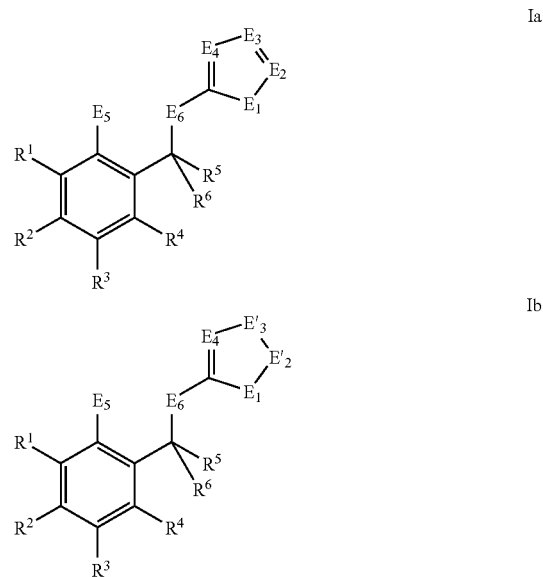

where, in the formula (Ia), $E_1$ is O, S, Se, Te, NR, $CR_2$, PR, preferably O or S, particularly preferably S, $E_3$ are each CR, N, P, preferably CR, $E_4$ is N, P, preferably N, $E_5$ is OH, SH, NHR, preferably OH or OR', SR', NRR', $E^6$ is NH, PH, preferably NH, or NR', PR', $R^5$, $R^6$ are each hydrogen or a linear, branched or cyclic alkyl radical or an aryl radical, $R^1$, $R^2$, $R^3$, $R^4$ are each hydrogen, a linear, branched or cyclic alkyl radical, an aryl radical, a halogen or a nitro group, R is hydrogen, a linear, branched or cyclic alkyl radical or an aryl radical, R' is a linear, branched or cyclic alkyl radical or an aryl radical, where at least one of the groups $E_5$ and $E_6$ contains a hydrogen atom and preference is given to both $E_5$ and $E_6$ each containing a hydrogen atom; and, in the formula (Ib), the symbols $E_1$, $E_4$, $E_5$, $E_6$, $R^5$, $R^6$, $R^6$, $R^1$, $R^2$, $R^3$, $R^4$, R and R' are as defined in formula (Ia)

and $E'_2$ and $E'_3$ are each O, S, Se, Te, NR, $CR_2$, PR, preferably $CR_2$.

In the compounds of the present invention of the formula Ia or Ib, preference is given to $E_1$ being S or O, particularly preferably S, and $E_4$ being N. Very particular preference is given to $E_1$ being S or O, preferably S, $E_4$ being N and $E_6$ being NH.

These compounds are very useful as ligands in transition metal complexes. The compounds of the present invention have a number of coordination sites. Thus, the transition metal centers of transition metal complexes can be stabilized by additional donor-acceptor interactions. These transition metal complexes are then very suitable for use in the polymerization of olefins.

The choice of substituents (electron-pushing or -withdrawing) on the heterocyclic 5-membered ring formed by $E_1$, $E_2$, $E_3$, $E_4$ and a further carbon atom enables the nucleophilicity of the metal center of a transition metal complex comprising the novel compounds of the formula Ia or Ib to be adjusted. When these transition metal complexes are used in the polymerization of polyolefins, the ligands can in this way be matched to the transition metal atoms used in each case or the monomers used in the polymerization.

Suitable linear or branched alkyl radicals are alkyl radicals having from 1 to 30 carbon atoms, preferably from 1 to 20 carbon atoms, e.g. methyl, ethyl, n-propyl, isopropyl, n-butyl, isobutyl, sec-butyl, tert-butyl, neopentyl and n-hexyl.

Suitable cyclic alkyl radicals are cyclic saturated hydrocarbon radicals having from 3 to 30 carbon atoms, preferably from 3 to 20 carbon atoms, e.g. cyclopropyl, cyclobutyl, cyclopentyl, cyclohexyl and adamantyl.

Suitable aryl radicals are aryl radicals having from 6 to 30 carbon atoms, preferably from 6 to 20 carbon atoms, e.g. phenyl, benzyl, naphthyl, biphenyl, terphenyl, phenanthryl and anthracenyl. The aryl radicals may also be alkyl-substituted. Suitable alkyl-substituted aryl radicals are tolyl, isopropylphenyl, t-butylphenyl, dimethylphenyl and di-t-butylphenyl.

In the abovementioned alkyl and aryl radicals, individual hydrogen atoms may be replaced by halogen atoms. Examples of such halogenated alkyl and aryl radicals are trifluoromethyl, pentafluorophenyl and chlorophenyl.

It is also possible for one or more hydrogen atoms in the alkyl and aryl radicals to be replaced by other hydrocarbon radicals, for example aryl-substituted alkyl radicals such as benzyl and cumyl.

Particular preference is given to $R^1$, $R^2$, $R^3$ and $R^4$ each being hydrogen, halogen, a nitro group or a linear or branched alkyl radical having from 1 to 20 carbon atoms, e.g. methyl, ethyl, n-propyl, isopropyl, n-butyl, isobutyl, sec-butyl, t-butyl, neopentyl or n-hexyl, very particularly preferably an alkyl radical having from 1 to 4 carbon atoms, e.g. methyl, ethyl, n-propyl, isopropyl, n-butyl, isobutyl, sec-butyl or t-butyl. Further preferred radicals $R^1$, $R^2$, $R^3$ and $R^4$ are aryl radicals having from 6 to 20 carbon atoms, e.g. phenyl, naphthyl, biphenyl, terphenyl, phenanthryl and anthracenyl, very particularly preferably phenyl and naphthyl, and also substituted aryl radicals such as tolyl and cumyl.

Very particular preference is given to at least one of the radicals $R^1$, $R^2$, $R^3$ and $R^4$ being a hydrogen atom; especial preference is given to two of the radicals mentioned being a hydrogen atom. The remaining radicals are preferably alkyl and/or aryl radicals, particularly preferably alkyl radicals, as mentioned above.

Corresponding definitions as for $R^1$, $R^2$, $R^3$ and $R^4$ likewise apply to the radicals $R^5$ and $R^6$ and also R. The abovementioned definitions for preferred alkyl and aryl radicals likewise apply to the radical R'.

Preferred definitions for $E_1$, $E_2$, $E'_2$, $E'_3$, $E_4$, $E_5$ and $E_6$ have likewise been mentioned above. Particular preference is given to compounds of the formula Ia or Ib in which $E_1$ is S or O, preferably S, and at the same time $E_4$ is N. $E_2$, and $E_3$ in compounds of the formula Ia are particularly preferably CR, with preferred definitions for R having been given above. In compound Ib, $E'_2$ and $E'_3$ are particularly preferably $CR_2$, where preferred definitions for R have likewise been given above and the two radicals bound to the carbon atom in $E'_2$ or $E'_3$ can be identical or different.

Very particular preference is given to compounds Ia and Ib having the following structural formulae,

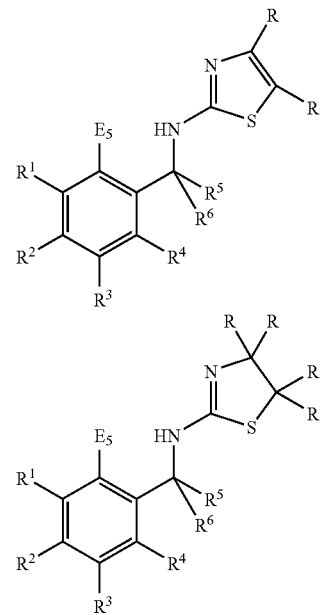

where $R^1$, $R^2$, $R^3$, $R^4$, $R^5$ and $R^6$ and also R are as defined above.

The compounds of the formulae Ia and Ib can be prepared by any method known to those skilled in the art. In a preferred embodiment, the compounds are prepared by reacting a compound of the formula IIa or IIb with a compound of the formula III to give a compound of the formula IVa or IVb. These compounds of the formula IVa and IVb, and also preferred compounds of these formulae are likewise subject matter of the present patent application.

To obtain the novel compounds of the formulae Ia and Ib from the compounds of the formulae IVa and IVb, the compounds of the formulae IVa and IVb are reduced.

The present invention therefore also provides a process for preparing compounds of the formulae Ia and Ib in which a compound of the formula IIa or IIb is reacted with a compound of the formula III to form a compound of the formula IVa or IVb (step a)). The compound of the formula IVa or IVb is subsequently reduced to give a compound of the formula Ia or Ib (step b)).

The reaction steps a) and b) are shown in the following scheme:

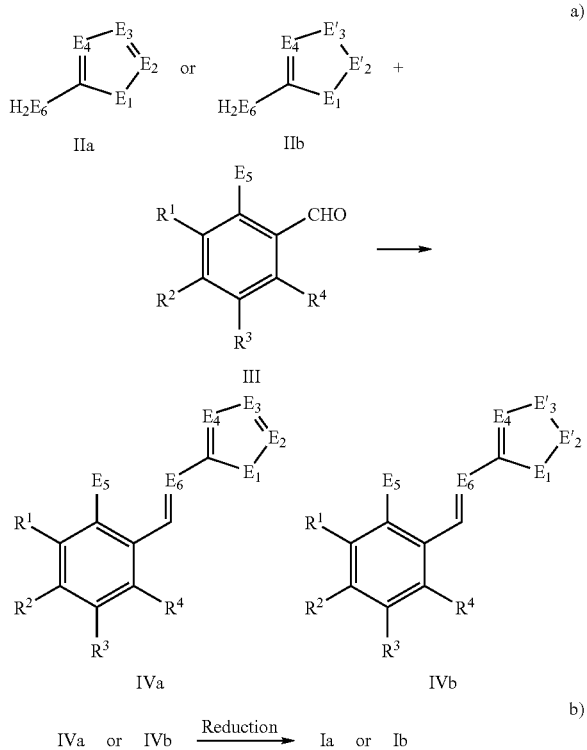

The symbols $E_1$, $E_2$, $E_3$, $E'_2$, $E'_3$, $E_4$, $E_5$, $E_6$, $R^5$, $R^6$, $R^1$, $R^2$, $R^3$, $R^4$, R and R' are as defined above.

The preparation of the compounds of the formulae Ia and Ib is preferably carried out in two steps, viz. step a) and step b), as mentioned above.

Step a):

Step a) is generally carried out in solution. Suitable solvents are alcohols such as methanol, ethanol and isopropanol and aromatic hydrocarbons such as toluene; preference is given to ethanol. In this step, the compound of the formula IIa or IIb together with one of the solvents mentioned is usually placed in a reaction vessel and, while stirring, the aldehyde of the formula III is added, preferably dropwise. In a preferred embodiment, the aldehyde of the formula III is likewise dissolved in one of the abovementioned solvents, preferably in the same solvent as that in which the compound of the formula IIa or IIb is initially charged. After the addition, catalytic amounts of a base of acid, preferably piperidine, pyridine or triethylamine or formic acid, sulfuric acid or toluene sulfonic acid, are added. The reaction solution is subsequently heated to, in general, from 10 to 150° C., preferably from 20 to 80° C., particularly preferably from 40 to 60° C. The reaction solution is generally heated for a period of from 0.5 to 36 hours, preferably from 1 to 16 hours, particularly preferably from 1 to 4 hours. The reaction mixture is subsequently cooled to from −60 to +30° C., preferably from 10 to 20° C. This generally results in precipitation of a solid which is separated off, preferably by filtration. Further product is obtained by reducing the volume of the mother liquor obtained after filtration by evaporation and once again cooling it to, in general, from −60 to +30° C., preferably from 10 to 20° C. The combined solids are subsequently dried, preferably under reduced pressure.

In the subsequent step b), the compounds of the formulae IVa and IVb obtained are reduced.

Step b)

The reduction of the compounds of the formula IVa or IVb can generally be carried out in any way known to those skilled in the art. Three different basic routes are conceivable for the reduction:

i) reduction to form compounds of the formulae Ia and Ib in which $R^5$ and $R^6$ are each hydrogen, ii) reduction to give compounds of the formulae Ia and Ib in which one of $R^5$ and $R^6$ is hydrogen and the other is a linear, branched or cyclic alkyl radical or an aryl radical, iii) reduction to form compounds of the formulae Ia and Ib in which both $R^5$ and $R^6$ are, independently of one another, linear, branched or cyclic alkyl radicals or aryl radicals.

Route i):

The reduction is generally carried out using any reducing agent known to those skilled in the art. Suitable reducing agents are $NaBH_4$ and $LiAlH_4$. The reduction is generally carried out in a solvent, preferably in methanol, tetrahydrofuran or diethyl ether. The molar ratio of the compound of the formula IVa or IVb to the reducing agent used is generally from 1:1 to 1:1000, preferably from 1:2 to 1:20. The reaction time is generally from 0.5 to 12 hours, preferably from 1 to 2 hours. The work-up of the reaction mixture to isolate the desired product is carried out by methods known to those skilled in the art.

Route ii):

To prepare the compounds of the formulae Ia and Ib by route ii), the compounds of the formulae IVa and IVb are reacted with metal alkyls. Suitable metal alkyls depend on the desired radicals $R^5$ and $R^6$. Preference is given to using methyllithium or butyllithium. In general, the reaction is carried out in a solvent, preferably tetrahydrofuran or diethyl ether. The molar ratio of the compound of the formula IVa or IVb to the metal alkyl is generally from 1:0.5 to 1:100, preferably from 1:1 to 1:2. The reaction is generally carried out at from −80 to +80° C., preferably from −30 to +20° C. It is usual to add a solution of the metal alkyl dropwise to a solution of a compound of the formula IVa or IVb. The reaction mixture is then usually warmed slowly to room temperature and generally stirred for another 1-8 hours, preferably 1-2 hours. This is followed by hydrolysis, preferably while cooling in ice, with equimolar amounts of an alcohol, preferably methanol. The desired compound of the formula Ia or Ib is subsequently isolated by methods known to those skilled in the art. The crude product obtained is subsequently recrystallized, preferably from a nonpolar solvent, for example pentane.

Route iii):

To prepare compounds of the formula Ia and Ia, in which both $R^5$ and $R^6$ are each a linear, branched or cyclic alkyl radical or aryl radical, compounds of the formulae IV'a and IV'b are used as starting materials instead of compounds of the formulae IVa and IVb. The compounds of the formulae IV'a and IV'b can be obtained by reaction of compounds of the formulae IIa and IIb with ketones of the formula III':

where R'''' is a linear, branched or cyclic alkyl radical or an aryl radical, preferably a linear $C_1$-$C_4$-alkyl radical.

These compounds of the formulae IV'a and IV'b, which are likewise subject matter of the present patent application, are reacted with further metal alkyl. The reaction is preferably carried out as described in route ii).

The ligands of the present invention are suitable for preparing metal complexes. An advantage of the ligands of the present invention is that the group $E_4$ gives an additional coordination site in the ligand which is not present in the ligands customarily used. This produces an additional donor-acceptor interaction which can stabilize the metal center in a corresponding metal complex. It is particularly advantageous that the nucleophilicity of the metal center can be adjusted by choice of the groups $E_1$, $E_2$ or $E'_2$, $E_3$ or $E'_3$ and $E_4$ (electron-pushing or electron-withdrawing). In this way, the ligands can be matched to particular metal atoms.

The present invention therefore also provides for the use of a novel compound of the formula Ia or Ib for preparing metal complexes.

The present invention further provides a metal complex of the formula V $$L_x MR''_y Y_z \quad (V)$$

where

L is a monoanionic or dianionic ligand derived from a compound of the formula Ia or Ib according to the present invention, where, in the case of a dianionic ligand, $E_5$ is O, S, RN, preferably O, and $E_6$ is N, P, preferably N, and, in the case of a monoanionic ligand, either $E_5$ is O, S, RN, preferably O, and $E_6$ is NR, PR, preferably NR, or $E_5$ is OR, SR, NRR', preferably SR, and $E_6$ is N, P, preferably N, and the further symbols $E_1$, $E_2$, $E'_2$, $E_3$, $E'_3$, $E_4$, $R^5$, $R^6$, $R^1$, $R^2$, $R^3$, $R^4$, R and R' in the formulae Ia and Ib are as defined above;

and, when

L is a dianionic ligand,

M is Ti, Zr, Hf, V, Nb, Ta, Cr, Mo, W, preferably Ti, Zr, Hf,

R'' is hydrogen, a hydrocarbon radical, preferably a linear, branched or cyclic alkyl radical as defined above, $NR'''_2$, OR''', halogen, acetylacetonate, preferably halogen, OR''', where R''' is hydrogen or a linear or branched or cyclic alkyl radical or aryl radical, where suitable linear, branched or cyclic alkyl radicals and aryl radicals have been mentioned above, Y is a Lewis base selected from the group consisting of tetrahydrofuran, diethyl ether, pyridine and triethylamine, x is 1 or 2, preferably 1, y is from 1 to 4, preferably 2, z is from 0 to 2, preferably 0 where R'' and Y may be joined to form a joint radical, for example via an alkylene group, and 2x+y corresponds to the valence of M;

or, when

L is a monoanionic ligand,

M is Ti, Zr, Hf, V, Nb, Ta, Cr, Mo, W, Ni, Pd, Co, Fe, Cu, Ru, Rh, preferably Ti, Zr, Hf, Pd, Ni, R'' is hydrogen, a hydrocarbon radical, preferably a linear, branched or cyclic alkyl radical as defined above, $NR'''_2$, OR''', halogen, acetylacetonate, preferably halogen, OR''', where R''' is hydrogen or a linear, branched or cyclic alkyl radical or aryl radical, where preferred linear, branched or cyclic alkyl radicals or aryl radicals have been mentioned above, Y is a Lewis base selected from the group consisting of tetrahydrofuran, diethyl ether, pyridine and triethylamine, x is 1, 2 or 3, preferably 1 or 2, y is from 1 to 4, z is from 0 to 2, preferably 0, where R'' and Y may be joined to form a joint radical, for example via an alkylene group, and x+y corresponds to the valence of M.

The ligand L in the metal complex of the present invention is particularly preferably a dianionic ligand, and the metal complex is very particularly preferably a complex in which L is a dianionic ligand and M is Ti, Zr or Hf, with Ti, Zr and Hf very particularly preferably being present in the oxidation state IV. In a preferred embodiment of these very particularly preferred metal complexes in which L is a dianionic ligand and M is Ti, Zr or Hf, very particularly preferably in the oxidation state IV, x is 1, y is 2 and z is 0.

In a further embodiment of the process of the present invention, the metal complex according to the present invention has at least one monoanionic ligand L and M is preferably Ti, Zr, Hf, Ni or Pd. When M is Ti, Zr or Hf, preferably in the oxidation state IV, x is preferably 2, y is preferably 2 and z is preferably 0 or x is preferably 1, y is preferably 3 and z is preferably 0. When M is Ni or Pd, particularly preferably in the oxidation state 2, x is preferably 1, y is preferably 1 and z is preferably 0.

Very particular preference is given to metal complexes of the following formulae:

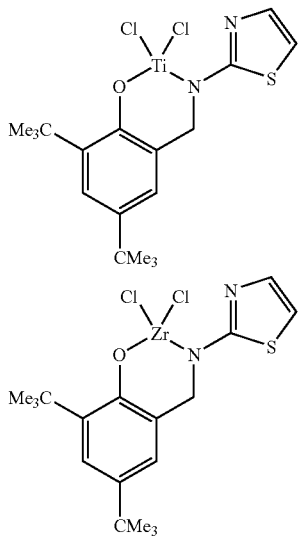

The metal complexes of the present invention are generally obtained by deprotonation of a compound of the formula Ia or Ib with a base and subsequent reaction with a metal compound, or by direct reaction of a compound of the formula Ia or Ib with a metal compound, where the metal compound contains a metal M selected from the group consisting of Ti, Zr, Hf, V, Nb, Ta, Cr, Mo and W, preferably Ti, Zr, Hf, when L is a dianionic ligand or a metal M selected from the group consisting of Ti, Zr, Hf, V, Nb, Ta, Cr, Mo, W, Ni, Pd, Co, Fe, Cu, Ru and Rh, preferably Ti, Zr, Hf, Ni, Pd, when L is a monoanionic ligand.

Suitable metal compounds are compounds of the formula VI $$MX_k \qquad (VI)$$

In this formula, M is a metal selected from the group consisting of Ti, Zr, Hf, V, Nb, Ta, Cr, Mo and W, preferably Ti, Zr and Hf, when a dianionic ligand is used as ligand L or, when L is a monoanionic ligand, M is selected from the group consisting of Ti, Zr, Hf, V, Nb, Ta, Cr, Mo, W, Ni, Pd, Co, Fe, Cu, Ru and Rh, preferably Ti, Zr, Hf, Ni and Pd.

k is a number corresponding to the oxidation state of M, in particular a number from 0 to 6. Thus, for example, k is 2 when a metal in the oxidation state II is used, k is 3 when a metal in the oxidation state III is used, k is 4 when a metal in the oxidation state IV is used, and so forth. Particular preference is given to k=4 when Ti(IV), Zr(IV) or Hf(IV) is used and k=3 when Ti(III) is used. k is preferably 2 when Ni(II) or Pd(II) is used.

X in the formula VI is hydrogen, halogen, hydrocarbon, an oxygen-containing group, a sulfur-containing group, a nitrogen-containing group, a boron-containing group, an aluminum-containing group, a phosphorus-containing group, a halogen-containing group, a heterocyclic radical, a silicon-containing group, a germanium-containing group or a tin-containing group.

Suitable halogen atoms are fluorine, chlorine, bromine and iodine.

Suitable hydrocarbon radicals are the same radicals mentioned above for $R^1$, $R^2$, $R^3$ and $R^4$.

Suitable heterocyclic radicals are nitrogen-containing heterocycles such as pyrroles, pyridines, pyrimidines quinolines and triazines, oxygen-containing compounds such as furan and pyran, sulfur-containing compounds such as thiophene, with one or more hydrogen atoms in these heterocyclic compounds being able to be replaced by alkyl groups or alkoxy groups.

Suitable oxygen-containing groups are, for example, hydroxy groups, alkoxy groups such as methoxy, ethoxy, propoxy and butoxy, aryloxy groups such as phenoxy, methyl phenoxy, dimethylphenoxy and naphthoxy, arylalkoxy groups such as phenylmethoxy and phenylethoxy, acetoxy groups and carbonyl groups.

Suitable sulfur-containing groups are, for example, sulfonato groups such as methylsulfonato, trifluoromethanesulfonato, phenylsulfonato, benzylsulfonato, p-toluene-sulfonato, trimethylbenzenesulfonato, triisobutylbenzenesulfonato, p-chlorobenzene-sulfonato and pentafluorobenzenesulfonato, sulfinato groups such as methylsulfinato, phenylsulfinato, benzylsulfinato, p-toluenesulfinato, trimethylbenzene-sulfinato and pentafluorobenzenesulfinato, alkylthio groups and arylthio groups.

Suitable nitrogen-containing groups are, for example, amino groups, alkylamino groups, such as methylamino, dimethylamino, diethylamino, dipropylamino, dibutylamino and dicyclohexylamino and arylamino or alkylarylamino groups such as phenylamino, diphenylamino, ditolylamino, dinaphthylamino and methylphenylamino.

Suitable boron-containing groups are, for example, $BR''''_4$, where R'''' is, for example, hydrogen, an alkyl group, an aryl group or a halogen atom.

Suitable phosphorus-containing groups are trialkylphosphine groups such as trimethylphosphine, tributylphosphine and tricyclohexylphosphine, triarylphosphine groups such as triphenylphosphine and tritolylphosphine, phosphite groups such as methyl phosphite, ethyl phosphite and phenyl phosphite, phosphonic acid groups and phosphoric acid groups.

Suitable silicon-containing groups are, for example, hydrocarbon-substituted silyl groups such as phenylsilyl, diphenylsilyl, trimethylsilyl, triethylsilyl, tripropylsilyl, tricyclohexylsilyl, triphenylsilyl, methyldiphenylsilyl, tritolylsilyl and trinaphthylsilyl, hydrocarbon-substituted silyl ether groups such as trimethylsilyl ether, silicon-substituted alkyl groups such as trimethylsilylmethyl and silicon-substituted aryl groups such as trimethylsilylphenyl.

Suitable germanium-containing groups are, for example, groups in which silicon in the silicon-containing compounds mentioned has been replaced by germanium.

Suitable tin-containing compounds are, for example, compounds in which silicon in the silicon-containing compounds mentioned has been replaced by tin.

Suitable halogen-containing groups are fluorine-containing groups such as $PF_6$, chlorine-containing groups such as $ClO_4$ and $SbCl_6$ and iodine-containing groups such as $IO_4$.

Suitable aluminum-containing compounds are $AlR''''_4$, where R'''' is, for example, hydrogen, an alkyl group or an aryl group which may be substituted.

Particularly preferred groups X are halogen atoms such as chlorine and bromine, preferably chlorine, alkyl groups such as methyl, alkoxy groups such as propoxy (in particular i-propoxy), alkylamino groups such as dimethylamino and hydrocarbon groups such as cyclopentadienyl radicals which may be substituted by one or more alkyl groups, in particular methyl or tert-butyl.

It is possible for the metal compound to contain a plurality of different groups X from among those mentioned. Particularly preferred metal compounds are Ti(NMe$_2$)$_4$, (tert-BuCp) TiCl$_3$, Ti(NMe$_2$)$_2$Cl$_2$, Ti(Oi-Pr)$_4$ and the corresponding Hf and Zr compounds (Cp=cyclopentadienyl). Further suitable compounds are TiCl$_3$, TiCl$_4$, Ti(CH$_2$C$_6$H$_5$)$_4$, Ti(NMe$_3$)$_4$ and the corresponding Zr and Hf compounds. NiCl$_2$, NiBr$_2$, PdCl$_2$ and PdBr$_2$ are also suitable. It is also possible to use complexes of the metal compounds mentioned with THF (tetrahydrofuran), acetonitrile or diethyl ether.

The molar ratio of the compound of the formula Ia or Ib used according to the present invention to the metal compound of the formula VI is generally 0.5-2:1, preferably 1-1.2:1.

Preparation of the novel metal complexes of the formula V by deprotonation of a compound of the formula Ia or Ib and subsequent reaction with a metal compound:

The base used for deprotonating the compound of the formula Ia or Ib is selected from the group consisting of metal alkyls, for example n-butyllithium, and metal hydrides, e.g. sodium hydride. The amount of base used depends on whether a monoanionic or dianionic ligand is being prepared from the compounds of the formula Ia or Ib. In the case of the preparation of a monoanionic ligand, the ratio of the compound of the formula Ia or Ib to the base used (molar ratio) is 1:0.5-1.5, preferably 1:1. In the case of the preparation of a dianionic ligand, the ratio of the compound of the formula Ia or Ib to the base used (molar ratio) is generally 1:1-3, preferably 1:1-2.

The deprotonation is carried out by methods known to those skilled in the art in an inert gas atmosphere. The deprotonation is generally carried out in a solvent selected from the group consisting of ether, tetrahydrofuran and toluene. The solvents required are generally dried before use. The base is usually added dropwise to a solution of the compound of the formula Ia or Ib which has been cooled to, in general, from −60 to +10° C., preferably −20° C. The mixture is subsequently warmed slowly to room temperature. The subsequent work-up is carried out by methods known to those skilled in the art.

The metal salt obtained, preferably a lithium salt, is reacted with one of the abovementioned metal compounds of the formula VI. The ratio of metal salt to metal compound is generally from 1:1 to 1:4, preferably from 1:1 to 1:2. The reaction is carried out by methods known to those skilled in the art, generally by placing the metal salt and the metal compound used in a reaction vessel and subsequently adding a nonpolar solvent, for example pentane, with cooling to, in general, from −60 to +20° C., preferably −20 to 0° C. After subsequently warming the reaction mixture to room temperature and stirring it for a further period, precipitated metal salt formed is generally filtered off and the desired metal complex is isolated.

Direct reaction of a compound of the formula Ia or Ib with a metal compound:

In the direct reaction, the metal compound of the formula VI is generally placed in a solvent, for example toluene, and a compound of the formula Ia or Ib, likewise dissolved in a solvent, is added dropwise at, in general, from −60 to +60° C., preferably from −20 to +20° C. The mixture is subsequently stirred further for a period of generally from 1 to 16 hours, preferably from 1 to 4 hours. The work-up is carried out by methods known to those skilled in the art. The entire reaction is carried out in an inert gas atmosphere.

The metal complexes of the present invention, which, owing to the ligands according to the present invention, have, in particular, a high stability, are very useful as polymerization catalysts, especially for the polymerization of olefins. The present invention therefore likewise provides for the use of the metal complexes of the present invention in the polymerization of olefins.

For the metal complexes of the present invention to have a sufficiently high catalytic activity in the polymerization of olefins, they are usually used together with a cocatalyst, so that the catalytically active species is formed "in-situ" from the metal complex.

The present invention therefore also provides a catalytically active composition comprising
a) a metal complex of the formula V according to the present invention as component A,
b) at least one compound, as component B, selected from the group consisting of
  1) an organometallic compound, as component B1,
  b2) an organoaluminum oxy compound, as component B2, and
  b3) a compound which reacts with the metal complex to form an ion pair, as component B3.

Component B

Component B1: Organometallic Compound

Suitable organometallic compounds (B1) which can be used in the catalytically active composition of the present invention include organometallic compounds containing at least one metal of groups I, II, XII and XIII of the Periodic Table of the Elements.

Examples of suitable organometallic compounds are organoaluminum compounds of the formula:

where $R^a$ and $R^b$ are each, independently of one another, a hydrocarbon radical having from 1 to 15 carbon atoms, preferably from 1 to 4 carbon atoms, Z is a halogen atom and m, n, p and q obey the following relationships: $0<m\leq 3$, $0\leq n<3$, $0\leq p<3$, $0\leq q<3$ and $m+n+p+q=3$.

Further suitable compounds are alkyl complexes containing a metal of group I and aluminum and having the formula:

where $M^2$ is Li, Na or K and $R^a$ is a hydrocarbon radical having from 1 to 15 carbon atoms, preferably from 1 to 4 carbon atoms.

Further suitable compounds are the alkyl compounds of metals of groups II and XII of the Periodic Table of the Elements which have the formula

where $R^a$ and $R^b$ are each, independently of one another, a hydrocarbon radical having from 1 to 15 carbon atoms, preferably from 1 to 4 carbon atoms, and $M^3$ is Mg Zn or Cd.

Examples of suitable organoaluminum compounds are organoaluminum compounds selected from the group consisting of tri-n-alkylaluminums such as trimethylaluminum, triethylaluminum, tri-n-butylaluminum, tripropylaluminum, tripentylaluminum, trihexylaluminum, trioctylaluminum and tridecylaluminum, branched trialkylaluminum compounds such as triisopropylaluminum, triisobutylaluminum, tri-sec-butylaluminum, tri-tert-butylaluminum, tri-2-methylbutylaluminum, tri-3-methylbutylaluminum, tri-2-methylpentylaluminum, tri-3-methylpentylaluminum, tri-4-methylpentylaluminum, tri-2-methylhexylaluminum, tri-3-methylhexylaluminum and tri-2-ethylhexylaluminum, tricycloalkylaluminum compounds such as tricyclohexylaluminum and tricycle-octylaluminum, triarylaluminum compounds such as triphenylaluminum and tritolylaluminum, dialkylaluminum hydrides such as diethylaluminum hydride and diisobutylaluminum hydride, trialkenylaluminum compounds, for example those of the formula $(i-C_4H_9)_x Al_y(C_5H_{10})_z$, where x, y and z are each a positive number and z is $\geq 2x$, e.g. isoprenylaluminum, alkylaluminum alkoxides such as isobutylaluminum methoxide, isobutylaluminum ethoxide and isobutylaluminum isopropoxide, dialkylaluminum alkoxides such as dimethylaluminum methoxide, dimethylaluminum ethoxide and dibutyl-aluminum butoxide, alkylaluminum sesquialkoxides such as ethylaluminum sesquiethoxide, butylaluminum sequibutoxide and partially alkoxylated alkylaluminum compounds having a mean composition corresponding to the formula $R^a_{2.5}Al(OR^b)_{0.5}$, where $R^a$ and $R^b$ are as defined above, dialkylaluminum aryloxides such as diethylaluminum phenoxide, diethylaluminum 2,6-di-t-butyl-4-methylphenoxide, ethylaluminum bis(2,6-di-t-butyl-4-methylphenoxide), diisobutylaluminum 2,6-di-t-butyl-4-methylphenoxide and isobutylaluminum bis(2,6-di-t-butyl-4-methylphenoxide), dialkylaluminum halides such as dimethylaluminum chloride, diethylaluminum chloride, dibutylaluminum chloride, diethylaluminum bromide and diisobutylaluminum chloride, alkylaluminum sesquihalides such as ethylaluminum sesquichloride, butylaluminum sesquichloride and ethylaluminum sesquibromide, partially halogenated alkylaluminum compounds such as ethylaluminum dichloride, propylaluminum dichloride and butylaluminum dibromide, dialkylaluminum hydrides such as diethylaluminum hydride and dibutylaluminum hydride, partially hydrogenated alkylaluminum compounds, for example alkylaluminum dihydrides such as ethylaluminum dihydride and propylaluminum dihydride, and partially alkoxylated and halogenated alkylaluminum compounds such as ethylaluminum ethoxide chloride, butylaluminum butoxide chloride and ethylaluminum ethoxide bromide.

Further suitable organoaluminum compounds are ones in which two or more aluminum compounds are combined, for example via a nitrogen atom, e.g. $(C_2H_5)_2AlN(C_2H_5)Al(C_2H_5)_2$.

Suitable alkyl complexes containing a metal of group I and aluminum are $LiAl(C_2H_5)_4$ and $LiAl(C_7H_{15})_4$.

Further suitable organometallic compounds (B1) include methyllithium, ethyllithium, propyllithium, butyllithium, methylmagnesium bromide, methylmagnesium chloride, ethylmagnesium bromide, ethylmagnesium chloride, propylmagnesium bromide, propylmagnesium chloride, butylmagnesium bromide, butylmagnesium chloride, dimethylmagnesium, diethylmagnesium, dibutylmagnesium and butylethylmagnesium.

Further suitable compounds are compounds which form the above-mentioned organoaluminum compounds during the polymerization, for example a combination of halogenated aluminum compounds and alkylmagnesium.

Particular preference is given to using organoaluminum compounds as organometallic compounds (B1).

The organometallic compounds (B1) can be used individually or as combinations of two or more of the compounds.

B2: Organoaluminum Oxy Compound

The organoaluminum oxy compounds (B2) which can be used in the catalytically active compositions of the present invention can be customary aluminoxanes or benzene-insoluble organoaluminum oxy compounds as are disclosed, for example, in JP-A 78687/1990.

Customary aluminoxanes can be prepared, for example, by the following method and are generally obtained as a solution in a hydrocarbon.

(i) Addition of an organoaluminum compound such as a trialkylaluminum to a suspension of a compound containing adsorbed water or a salt containing water of crystallization, for example magnesium chloride hydrate, copper sulfate hydrate, aluminum sulfate hydrate, nickel sulfate hydrate or cerium chloride hydrate, in a hydrocarbon, so that the organoaluminum compound can react with the adsorbed water or water of crystallization.

(ii) Reaction of an organoaluminum compound such as a trialkylaluminum with water, ice or water vapor in a solvent such as benzene, toluene, ethyl ether or tetrahydrofuran.

(iii) Reaction of an organotin oxide such as dimethyltin oxide or dibutyltin oxide with an organoaluminum compound such as a trialkylaluminum in a solvent such as decane, benzene or toluene.

The aluminoxane may contain small amounts of an organometallic compound. Furthermore, it is possible for the solvent or the unreacted organoaluminum compound to be distilled off from the aluminoxane solution obtained and the residue to be redissolved in a solvent or suspended in a liquid which is a poor solvent for aluminoxanes.

Suitable organoaluminum compounds which can be used for preparing the aluminoxanes are the same ones as have been described above as organoaluminum compounds (B1). Preference is given to trialkylaluminum compounds and tricycloalkylaluminum compounds. Particular preference is given to trimethylaluminum.

The organoaluminum compounds can be used individually or in combinations of two or more different compounds.

Suitable solvents for preparing the aluminoxanes include aromatic hydrocarbons such as benzene, toluene, xylene, cumene and cymene, aliphatic hydrocarbons such as pentane, hexane, heptane, octane, decane, dodecane, hexadecane and octadecane, alicyclic hydrocarbons such as cyclopentane, cyclohexane, cyclooctane and methylcyclopentane, petroleum fractions such as gasolene, kerosene and gas oil, and halogen compounds of these aromatic, aliphatic and alicyclic hydrocarbons, in particular chlorides and bromides thereof. Further suitable solvents are ethers such as ethyl ether and tetrahydrofuran. Particular preference is given to using aromatic hydrocarbons and aliphatic hydrocarbons.

The benzene-insoluble organoaluminum oxy compound is preferably an organoaluminum oxy compound comprising an Al component which is soluble in an amount of not more than 10%, preferably not more than 5%, particularly preferably not more than 2%, based on the Al atom, in benzene at 60° C. This means that the benzene-insoluble organoaluminum oxy compound is preferably insoluble or virtually insoluble in benzene.

Furthermore, it is possible to use, for example, organoaluminum oxy compounds containing boron, as are disclosed in EP-A 0 950 667.

The organoaluminum oxy compounds (B2) mentioned can be used individually or in combinations of two or more of these compounds.

B3: Compound which Reacts with the Metal Complex to Form an ion Pair

Suitable compounds are all compounds which form an ion pair on contact with the transition metal complex (A). Suitable compounds include Lewis acids, ionic compounds, borane compounds and carborane compounds, as disclosed in JP-A 501950/1989, JP-A 502036/1989, JP-A 179005/1991, JP-A 179006/1991, JP-A 207703/1991 and JP-A 207704/1991 and U.S. Pat. No. 5,321,106. Furthermore, it is possible to use heteropoly compounds and isopoly compounds.

Suitable Lewis acids are, for example, compounds of the formula $BR_3$, where R is fluorine or a phenyl group which may be substituted by fluorine, methyl or trifluoromethyl. Examples of suitable compounds are trifluoroboron, triphenylboron, tris(4-fluorophenyl)boron, tris(3,5-difluorophenyl)boron, tris(4-fluoromethylphenyl)boron, tris(pentafluorophenyl)boron, tris(p-tolyl)boron, tris(o-tolyl)boron and tris(3,5-dimethyl-phenyl)boron.

Suitable ionic compounds include compounds of the formula VII

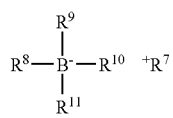

where $R^7$ is $H^+$, a carbonium cation, an oxonium cation, an ammonium cation, a phosphonium cation, a cycloheptyltrienyl cation or a ferrocenium cation containing a transition metal. $R^8$ to $R^{11}$ are each, independently of one another, an organic group, preferably an aryl group or a substituted aryl group.

$R^7$ is particularly preferably a carbonium cation or an ammonium cation, very particularly preferably triphenylcarbonium, N,N-dimethylanilinium or N,N-diethylanilium. Further suitable ionic compounds are trialkyl-substituted ammonium salts, N,N-dialkylanilinium salts, dialkylammonium salts and triarylphosphonium salts.

Suitable trialkyl-substituted ammonium salts are triethylammonium tetra(phenyl)borate, tripropylammonium tetra(phenyl)borate, tri(n-butyl)ammonium tetra(phenyl)borate, tri(n-butyl)ammonium tetra(pentafluorophenyl)borate, tripropylammonium tetra(o,p-dimethyl-phenyl)borate, tri(n-butyl)ammonium tetra(p-trifluoromethylphenyl)borate, tri(n-butyl)-ammonium tetra(3,5-ditrifluoromethylphenyl)borate and tri(n-butyl)ammonium tetra(o-tolyl)borate.

Suitable N,N-dialkylanilinium salts include N,N-dimethylanilinium tetra(phenyl)borate, N,N-diethylanilinium tetra(phenyl)borate and N,N-2,4,6-pentamethylanilinium tetra(phenyl)borate.

Suitable dialkylammonium salts include di(1-propyl)ammonium tetra-(pentafluoro-phenyl)borate and dicycloammonium tetra(phenyl)borate.

Further suitable ionic compounds are triphenylcarbenium tetrakis(pentafluoro-phenyl)borate, N,N-dimethylanilinium tetrakis(pentafluoro-phenyl)borate, and ferrocenium tetra(pentafluorophenyl)borate.

Further suitable compounds which react with the metal complex to form an ion pair are disclosed in EP-A 0 950 667. Very particular preference is given to using triphenyl-carbonium tetrakis(pentafluorophenyl)borate.

The catalytically active composition of the present invention comprising the components A and B can further comprise a support material as component C. Such supported catalytically active compositions are suitable, in particular, for use in gas-phase polymerization processes, very particularly preferably in gas-phase fluidized-bed polymerization processes.

Support Material, C

Both inorganic and organic compounds are suitable as support material.

Preferred inorganic compounds are porous oxides, inorganic chlorides, clay, clay minerals and sheet compounds.

Suitable porous oxides include $SiO_2$, $Al_2O_3$, MgO, Zro, $TiO_2$, $B_2O_3$, CaO, ZnO, BaO, $ThO_2$ and mixtures of compounds in which these oxides are present, e.g. natural or synthetic zeolites, $SiO_2$—MgO, $SiO_2$—$Al_2O_3$, $SiO_2$—$TiO_2$, $SiO_2$—$V_2O_5$, $SiO_2$—$Cr_2O_3$ and $SiO_2$—$TiO_2$—MgO. Particular preference is given to porous oxides comprising $SiO_2$ and/or $Al_2O_3$ as main components.

The inorganic oxides can also contain small amounts of carbonates, sulfates, nitrates or oxides.

The porous oxides which are used according to the present invention preferably have a particle diameter of from 10 to 300 μm, particularly preferably from 20 to 200 μm, and a specific surface area of generally from 50 to 1000 m²/g, preferably from 100 to 700 m²/g, and a pore volume of generally from 0.3 to 3 cm³/g. The support material can, if necessary, be calcined at, in general, from 100 to 1000° C., preferably from 150 to 700° C. before use.

Suitable inorganic oxides, clays, clay minerals and sheet compounds are disclosed, for example, in EP-A 0 950 667.

Suitable organic support materials are, for example, granular or particulate solid compounds having a particle diameter of generally from 10 to 300 μm. Examples of such compounds include (co)polymers which have been prepared by reaction of an α-olefin having from 2 to 14 carbon atoms, e.g. ethylene, propylene, 1-butene or 4-methyl-1-pentene, as main monomer, (co)polymers which have been prepared by reaction of vinylcyclohexane or styrene as main monomer and derivatives of the (co)polymers mentioned.

The catalytically active compositions of the present invention are very useful for the polymerization and copolymerization of olefins. Owing to the ligands which can be varied in many ways and are simple to prepare, it is possible to obtain many different metal complexes and thus many different catalytically active compositions which can be used for preparing tailored polymers or copolymers.

The present invention therefore also provides for the use of a catalytically active composition according to the present invention for the polymerization or copolymerization of olefins.

The present invention further provides a process for the polymerization or copolymerization of olefins, in which an olefin is polymerized in the presence of a catalytically active composition according to the present invention or at least two different olefins are copolymerized in the presence of a catalytically active composition according to the present invention.

The procedure for carrying out polymerization or copolymerization and suitable apparatuses for carrying out polymerization or copolymerization and suitable olefins are known to those skilled in the art.

Olefins which are preferably used are selected from the group consisting of α-olefins having from 2 to 20 carbon atoms, e.g. ethylene, propylene, 1-butene, 1-pentene, 3-methyl-1-butene, 1-hexene, 4-methyl-1-pentene, 3-methyl-1-pentene, 1-octene, 1-decene, 1-dodecene, 1-tetradecene, 1-hexadecene and 1-octadecene, cycloolefins having from 3 to 20 carbon atoms, e.g. cyclopentene, cycloheptene, norbornene, 5-methyl-2-norbornene and tetracyclododecene, polar monomers such as α,β-unsaturated carboxylic acids, e.g. acrylic acid, methacrylic acid, fumaric acid, maleic anhydride, itaconic acid, itaconic anhydride and bicyclo [2.2.1]-5-heptene-2,3-dicarboxylic acid, metal salts of these acids, e.g. sodium salts, potassium salts, lithium salts, zinc salts, magnesium salts and calcium salts, α,β-unsaturated carboxylic esters, e.g. methyl acrylate, ethyl acrylate, n-propyl acrylate, isopropyl acrylate, n-butyl acrylate, isobutyl acrylate, tert-butyl acrylate, 2-ethylhexyl acrylate, methyl methacrylate, ethyl methacrylate, n-propyl methacrylate, isopropyl methacrylate, n-butyl methacrylate and isobutyl methacrylate, vinyl esters, vinyl acetate, vinyl propionate, vinyl caproate, vinyl caprate, vinyl laurate, vinyl stearate and vinyl trifluoro acetate, unsaturated glycidyl esters and halogenated olefins such as vinyl chloride, vinyl fluoride and allyl fluoride.

Vinylcyclohexanes, dienes and polyenes can likewise be used as olefins. Suitable dienes and polyenes are cyclic or linear and have from 4 to 30 carbon atoms, preferably from 4 to 20 carbon atoms, and have two or more double bonds. Examples of suitable compounds are butadiene, isoprene, 4-methyl-1,3-pentadiene, 1,3-pentadiene, 1,4-pentadiene, 1,5-hexadiene, 1,4-hexadiene and 1,3-hexadiene.

Aromatic vinyl compounds can likewise be used as olefins. Examples of suitable aromatic vinyl compounds are styrene, monoalkylstyrenes and polyalkylstyrenes, e.g. o-methylstyrene, m-methylstyrene, p-methylstyrene, o,p-dimethylstyrene, o-ethylstyrene, m-ethylstyrene and p-ethylstyrene, styrene derivatives containing functional groups, e.g. methoxystyrene, ethoxystyrene, hydroxystyrene, o-chlorostyrene, p-chlorostyrene and divinylbenzene and also further compounds such as 3-phenylpropylene, 4-phenylpropylene and β-methylstyrene.

Further suitable α-olefins are disclosed, for example, in EP-A 0 950 667.

As α-olefins, preference is given to using ethylene and propylene, particularly preferably ethylene. The α-olefins can be used alone or in combinations of two or more different α-olefins. Further preferred olefins are styrene, isobutene, internal olefins such as 2-butene, cyclic olefins such as norbornene or cyclopentene and polar olefins such as acrylates.

It is also possible to copolymerize an α-olefin and a polar olefin, for example olefins which have been described above.

It is also possible to copolymerize an α-olefin as set forth in the present patent application and a nonconjugated diene or polyene. Examples of nonconjugated dienes and polyenes include 1,4-pentadiene, 1,5-hexadiene and 1,4-hexadiene.

It is likewise possible to use further monomers from among those mentioned in a copolymerization with α-olefins. The polymerization or copolymerization can be carried out by any methods known to those skilled in the art. Suitable orders of addition and processes are described, for example, in EP-A 0 950 667. Thus, it is possible to introduce the component (A) (metal complex) and at least one component (B) selected from among organometallic compounds (B1), organoaluminum oxy compounds (B2) and compounds which react with the metal complex to form an ion pair (B3) into the polymerization reactor in any order. It is likewise possible firstly to prepare a catalyst by bringing the components (A) and (B) into contact with one another and subsequently to introduce this into the polymerization reactor. Furthermore, a catalyst prepared by bringing the components (A) and (B) into contact with one another can be introduced together with further component (B) which may be different from the first component (B) into the polymerization reactor in any order. Furthermore, it is possible to introduce the metal complex (A) applied to a support material (C) and the component (B) into the polymerization reactor in any order. It is likewise possible for the components (A) and (B) to have been applied together to a support material (C) and to be introduced in this form into the polymerization reactor.

Furthermore, numerous further variants are conceivable, for example the variants disclosed in EP-A 0 950 667.

Furthermore, it is possible for the catalytically active compositions of the present invention to be used not alone but in combination with other catalytically active compositions of the same type or other polymerization catalysts, for example Phillips catalysts, Ziegler catalysts and/or metallocene catalysts which can each likewise be present in supported or unsupported form.

In a further embodiment of the present invention, the olefin can be prepolymerized on the solid catalyst components, with the metal complex (A) and, if desired, component (B) having been applied to a support (C).

The polymerization can be carried out as a solution polymerization, a suspension polymerization or as a gas-phase polymerization.

Suitable solvents for the solution polymerization are hydrocarbons, for example aliphatic hydrocarbons such as propane, butane, pentane, hexane, heptane, octane, decane, dodecane and kerocene, alicyclic hydrocarbons such as cyclopentane, cyclohexane and methylcyclopentane, aromatic hydrocarbons such as benzene, toluene and xylene, halogenated hydrocarbons such as ethylene chloride, chlorobenzene and dichloromethane and mixtures of the hydrocarbons mentioned. It is likewise possible for the olefin itself to be used as solvent.

The metal complex (A) is generally used in an amount of from $10^{-12}$ to $10^{-2}$ mol, preferably from $10^{-10}$ to $10^{-3}$ mol, per liter of reaction volume. According to the present invention, the olefin can be polymerized with a high polymerization activity even when the metal complex (A) is used in relatively low concentrations.

The component (B1) is generally used in such an amount that the molar ratio of the component (B1) to the transition metal atom (M) in the metal complex (A) is from 0.01 to 100 000, preferably from 0.05 to 50 000.

The component (B2) can be used in such an amount that the molar ratio of the aluminum atom in the component (B2) to the transition metal atom (M) in the metal complex (A) is generally from 10 to 500 000, preferably from 20 to 100 000.

The component (B3) can be used in such an amount that the molar ratio of the component (B3) to the transition metal atom (M) in the metal complex (A) is generally from 1 to 10, preferably from 1 to 5.

The polymerization temperature in the process of the present invention is generally from −50 to 200° C., preferably from 0 to 170° C. The polymerization pressure is generally from atmospheric pressure to 100 bar, preferably from atmospheric pressure to 50 bar. The polymerization can be carried out batchwise, semicontinuously or continuously. It is likewise possible to carry out the polymerization in two or more separate steps under different reaction conditions.

The molecular weight of the olefin (co)polymers obtained can be regulated by the presence of hydrogen in the polymerization system or by alteration of the polymerization temperature. It is also possible to regulate the molecular weight by altering the type of component (B).

The process of the present invention thus makes it possible to obtain numerous polymers and copolymers whose properties differ depending on the type of catalytically active compositions used and the reaction conditions. The present invention therefore further provides polymers or copolymers which can be prepared by the process of the present invention.

The following examples illustrate the invention.

EXAMPLES

1. General

Owing to the sensitivity of the metal complexes to oxidation and hydrolysis, all experiments on preparation of the metal complexes and also the polymerization tests were carried out under an inert gas atmosphere using the Schlenk technique. The solvents required for this purpose were dried before use. The starting compounds for preparation of the ligands and also NaBH$_4$, Ti(Oi-Pr)$_4$ and the BuLi, MeLi and MgCl(CH$_2$Ph) solutions were procured from Acros or Aldrich and were used without additional purification steps. The further metal precursors used were prepared by the methods described in the literature. Activation of the complexes for the polymerization experiments was carried out using an MAO solution in toluene having an aluminum content of 10% or 7%.

2. Synthesis of the Ligands

2.1 Preparation of the Thiazolyliminomethylphenols

A solution of hydroxybenzaldehyde in ethanol was added dropwise to a solution of an aminothiazole in ethanol at room temperature while stirring. After the addition was complete, a few drops of piperidine were added and the reaction solution was refluxed for 2 hours. It was subsequently cooled to 0° C. The yellow solid which precipitated was filtered off. Evaporation of the mother liquor to a smaller volume and cooling to −30° C. resulted in precipitation of further product. The combined fractions were dried under reduced pressure.

2.1.1 4,6-Di-tert-butyl-2-(thiazol-2'-yliminomethyl)phenol (1)

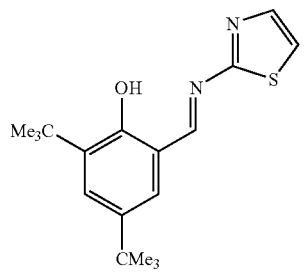

Starting materials:
  2.71 g (27.1 mmol) of 2-aminothiazol in 30 ml of EtOH
  6.35 g (27.1 mmol) of 3,5-di-tert-butyl-2-hydroxybenzaldehyde in 40 ml of EtOH
  80 mg of piperidine
  Yield: 68% (5.87 g, 18.5 mmol)
  $^1$H-NMR (400 MHz, C$_6$D$_6$): δ=1.21 (s, 9H, C4-C(CH$_3$)$_3$), 1.59 (s, 9H, C6-C(CH$_3$)$_3$), 6.43 (d, $^3J_{HH}$=3.6 Hz, 1H, NCH=CHS), 6.94 (d, $^4J_{HH}$=2.4 Hz, 1H, C5-H), 7.36 (d, $^3J_{HH}$=3.6 Hz, 1H, NCH=CHS), 7.58 (d, $^4J_{HH}$=2.4 Hz, 1H, C3-H), 9.14 (s, 1H, CH=N), 13.29 (s, 1H, OH).

2.1.2 4,6-Di-tert-butyl-2-(4'-methylthiazol-2'-yliminomethyl)phenol (2)

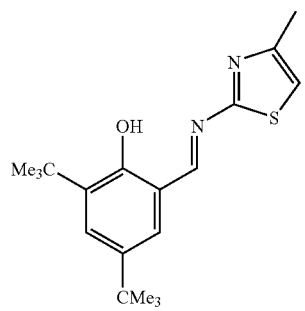

Starting materials:
  3.90 g (34.1 mmol) of 2-amino-4-methylthiazol in 30 ml of EtOH
  8.00 g (34.1 mmol) of 3,5-di-tert-butyl-2-hydroxybenzaldehyde in 40 ml of EtOH
  100 mg of piperidine
  Yield: 76% (8.56 g, 25.9 mmol)
  $^1$H-NMR (400 MHz, C$_6$D$_6$): δ=1.22 (s, 9H, C4-C(CH$_3$)$_3$), 1.59 (s, 9H, C6-C(CH$_3$)$_3$), 2.20 (s, 3H, CH$_3$), 6.14 (s, 1H, NC(CH$_3$)=CHS), 6.95 (d, $^4J_{HH}$=2.4 Hz, 1H, C5-H), 7.59 (d, $^4J_{HH}$=2.4 Hz, 1H, C3-H), 9.17 (s, 1H, CH=N), 13.36 (s, 1H, OH).

2.1.3 4,6-Di-tert-butyl-2-(5'-methylthiazol-2'-yliminomethyl)phenol (3)

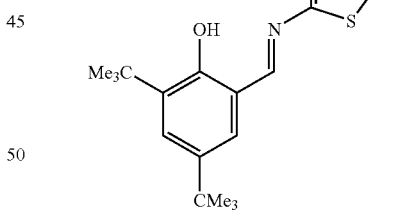

Starting materials:
  3.90 g (34.1 mmol) of 2-amino-5-methylthiazol in 30 ml of EtOH
  8.00 g (34.1 mmol) of 3,5-di-tert-butyl-2-hydroxybenzaldehyde in 40 ml of EtOH
  100 mg of piperidine
  Yield: 80% (9.00 g, 27.2 mmol)
  $^1$H-NMR (400 MHz, C$_6$D$_6$): δ=1.21 (s, 9H, C4-C(CH$_3$)$_3$), 1.59 (s, 9H, C6-C(CH$_3$)$_3$), 1.82 (s, 3H, CH$_3$), 6.96 (d, $^4J_{HH}$=2.4 Hz, 1H, C3-H), 7.10 (s, 1H, NCH=C(CH$_3$)S), 7.59 (d, $^4J_{HH}$=2.4 Hz, 1H, C5-H), 9.18 (s, 1H, CH=N), 13.36 (s, 1H, OH).

2.1.4 4,6-Di-tert-butyl-2-(benzothiazol-2'-yliminomethyl)phenol (4)

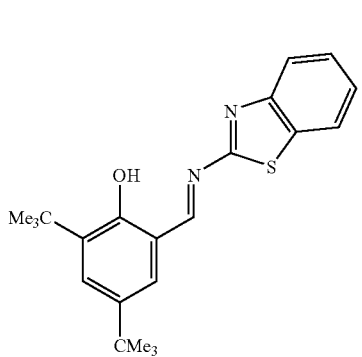

Starting materials:
  5.13 g (34.1 mmol) of 2-aminobenzothiazol in 30 ml of EtOH
  8.00 g (34.1 mmol) of 3,5-di-tert-butyl-2-hydroxybenzaldehyde in 40 ml of EtOH
  100 mg of piperidine
  Yield: 71% (8.87 g, 24.2 mmol)
  $^1$H-NMR (400 MHz, C$_6$D$_6$): δ=1.22 (s, 9H, C4-C(CH$_3$)$_3$), 1.58 (s, 9H, C6-C(CH$_3$)$_3$), 6.94 (d, $^4J_{HH}$=2.0 Hz, 1H, C3-H), 6.97 (t, $^3J_{HH}$=7.6 Hz, 1H, benzothiazolyl-C6-H), 7.18 (1H, benzothiazolyl-C5-H), 7.32 (d, $^3J_{HH}$=7.6 Hz, 1H, benzothiazolyl-C7-H), 7.61 (d, $^4J_{HH}$=2.0 Hz, 1H, C5-H), 8.00 (d, $^3J_{HH}$=8.0 Hz, 1H, benzothiazolyl-C4-H), 9.15 (s, 1H, CH=N), 13.29 (s, 1H, OH).

2.2 Reduction of the Thiazolyliminomethylphenols

NaBH$_4$ was added a little at a time to a solution of a thiazolyliminomethylphenol in methanol at room temperature while stirring. After the addition was complete, the mixture was stirred for another 1 hour. During this time, the reaction mixture decolorized and a colorless solid was precipitated. The product was filtered off and dried under reduced pressure.

2.2.1 [Lig1]H$_2$ (5) (Reduction of Compound (1) from Example 2.1.1)

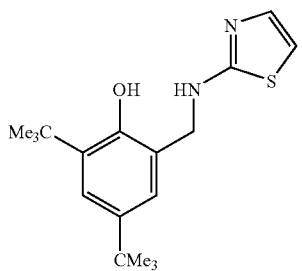

Starting materials:
  1.47 g (4.64 mmol) of 1 in 10 ml of MeOH
  292 mg (7.72 mmol) of NaBH$_4$
  Yield: 85% (1.26 g, 3.96 mmol)
  $^1$H-NMR (400 MHz, C$_6$D$_6$): δ=1.40 (s, 9H, C4-C(CH$_3$)$_3$), 1.68 (s, 9H, C6-C(CH$_3$)$_3$), 4.03 (s, 3H, CH$_2$NH), 5.73 (d, $^3J_{HH}$=3.6 Hz, 1H, NCH=CHS), 6.72 (d, $^3J_{HH}$=3.6 Hz, 1H, NCH=CHS), 6.91 (d, $^4J_{HH}$=2.4 Hz, 1H, C3-H), 7.52 (d, $^4J_{HH}$=2.4 Hz, 1H, C5-H), 11.2 (s, 1H, OH).

2.2.2 [Lig2]H$_2$ (6) (Reduction of Compound (2) from Example 2.1.2)

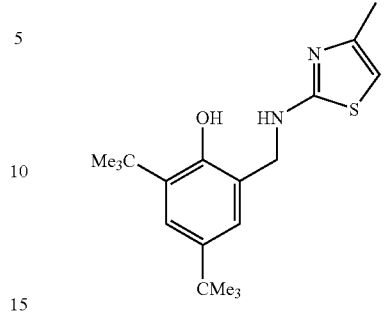

Starting materials:
  8.31 g (25.1 mmol) of 2 in 80 ml of MeOH
  1.6 g (42.3 mmol) of NaBH$_4$
  Yield: 81% (6.79 g, 20.4 mmol)
  $^1$H-NMR (400 MHz, C$_6$D$_6$): δ=1.40 (s, 9H, C4-C(CH$_3$)$_3$), 1.68 (s, 9H, C6-C(CH$_3$)$_3$), 2.07 (s, 3H, CH$_3$), 4.01 (d, $^3J_{HH}$=6.0 Hz, 2H, CH$_2$), 4.07 (t, $^3J_{HH}$=6.0 Hz, 1H, NH), 5.41 (s, 1H, NC(CH$_3$)=CHS), 6.93 (d, $^4J_{HH}$=2.6 Hz, 1H, C3-H), 7.52 (d, $^4J_{HH}$=2.6 Hz, 1H, C5-H), 11.42 (s, 1H, OH).

2.2.3 [Lig3]H$_2$ (7) (Reduction of Compound (3) from Example 2.1.3)

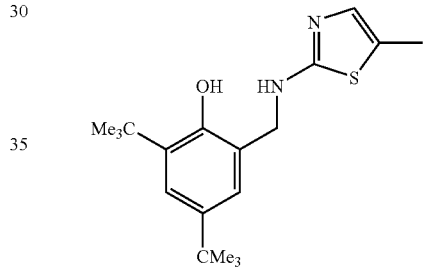

Starting materials:
  8.89 g (26.9 mmol) of 3 in 80 ml of MeOH
  1.63 g (43.1 mmol) of NaBH$_4$
  Yield: 82% (7.30 g, 21.9 mmol)
  $^1$H-NMR (400 MHz, C$_6$D$_6$): δ=1.41 (s, 9H, C4-C(CH$_3$)$_3$), 1.70 (s, 3H, CH$_3$), 1.71 (s, 9H, C6-C(CH$_3$)$_3$), 3.95 (t, 1H, NH), 4.04 (d, $^3J_{HH}$=6.4 Hz, 2H, CH$_2$), 6.42 (s, 1H, NCH=C(CH$_3$)S), 6.93 (d, 1H, $^4J_{HH}$=2.4 Hz, C3-H), 7.53 (d, $^4J_{HH}$=2.4 Hz, 1H, C5-H), 11.31 (s, 1H, OH).

2.2.4 [Lig4]H$_2$ (8) (Reduction of Compound (4) from Example 2.1.4)

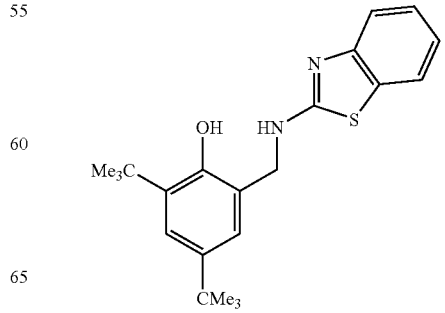

Starting materials:
  5.85 g (15.9 mmol) of 4 in 40 ml of MeOH
  0.97 g (25.6 mmol) of NaBH$_4$
  Yield: 68% (3.98 g, 10.8 mmol)

$^1$H-NMR (400 MHz, C$_6$D$_6$): δ=1.42 (s, 9H, C4-C(CH$_3$)$_3$), 1.69 (s, 9H, C6-C(CH$_3$)$_3$), 4.06 (m, 3H, CH$_2$, NH), 6.81 (t, $^3J_{HH}$=7.6 Hz, 1H, benzothiazolyl-C6-H), 6.93 (d, $^4J_{HH}$=2.4 Hz, C3-H), 7.04 (t, $^3J_{HH}$=7.6 Hz, 1H, benzothiazolyl-C5-H), 7.10 (d, $^3J_{HH}$=7.6 Hz, 1H, benzothiazolyl-C7-H), 7.52 (d, $^4J_{HH}$=2.4 Hz, 1H, C5-H), 7.63 (d, $^3J_{HH}$=7.6 Hz, 1H, benzothiazolyl-C4-H), 11.31 (s, 1H, OH).

2.3 Reactions of the Thiazolyliminomethylphenols with Metal Alkyls

The solution of the metal alkyl was added dropwise to a solution of the imine at −70° C. while stirring. The reaction mixture was slowly warmed to room temperature and stirred for another 15 hours. It was then carefully hydrolyzed with an equimolar amount of methanol while cooling in ice. Dilute aqueous NH$_4$Cl solution was subsequently added. The phases were separated. After the ether phase had been dried over MgSO$_4$, the solvent was removed under reduced pressure. The crude product was recrystallized from pentane.

2.3.1 [Lig5]H$_2$ (9) (Reaction of Compound (1) from Example 2.1.1)

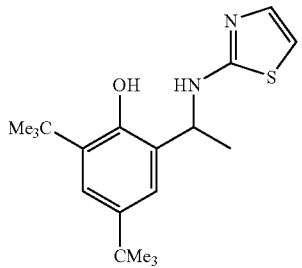

Starting materials:
  0.50 g (1.58 mmol) of 1 in 35 ml of Et$_2$O
  2.0 ml (3.20 mmol) of 1.6 M MeLi solution in Et$_2$O
  Yield: 92% (422 mg, 1.46 mmol)

$^1$H-NMR (400 MHz, C$_6$D$_6$): δ=1.01 (d, $^3J_{HH}$=7.2 Hz, 3H, CH$_3$), 1.38 (s, 9H, C4-C(CH$_3$)$_3$), 1.71 (s, 9H, C6-C(CH$_3$)$_3$), 4.07 (d, 1H, NH), 5.23 (quin, 1H, CH(NH)(CH$_3$)), 5.73 (d, $^3J_{HH}$=3.6 Hz, 1H, NCH=CHS), 6.73 (d, $^3J_{HH}$=3.6 Hz, 1H, NCH=CHS), 7.09 (d, $^4J_{HH}$=2.4 Hz, 1H, C3-H), 7.49 (d, $^4J_{HH}$=2.4 Hz, 1H, C5-H), 10.94 (s, 1H, OH).

2.3.2 [Lig6]H$_2$ (10) (Reaction of Compound (1) from Example 2.1.1)

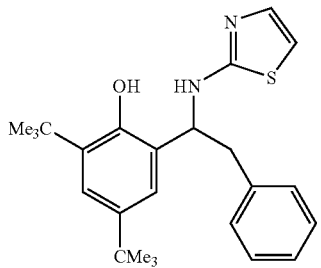

Starting materials:
  1.00 g (3.16 mmol) of 1 in 35 ml of Et$_2$O
  7.0 ml (7.0 mmol) of 1 M MgCl(CH$_2$Ph) solution in Et$_2$O
  Yield: 85% (1.10 g, 2.69 mmol)

$^1$H-NMR (400 MHz, C$_6$D$_6$): δ=1.42 (s, 9H, C4-C(CH$_3$)$_3$), 1.69 (s, 9H, C6-C(CH$_3$)$_3$), 2.83 (d, $^3J_{HH}$=7.6 Hz, 2H, CH$_2$Ph), 4.38 (d, $^3J_{HH}$=6.4 Hz, 1H, NH), 5.45 (quart, $^3J_{HH}$=7.2 Hz, 1H, CH(NH)(CH$_2$Ph)), 5.65 (d, $^3J_{HH}$=3.6 Hz, 1H, NCH=CHS), 6.67 (d, $^3J_{HH}$=3.6 Hz, 1H, NCH=CHS), 6.87 (d, $^3J_{HH}$=7.2 Hz, 2H, ortho CH$_2$C$_6$H$_5$), 6.92 (t, $^3J_{HH}$=7.2 Hz, 1H, para CH$_2$C$_6$H$_5$), 6.70 (t, $^3J_{HH}$=7.2 Hz, 2H, meta CH$_2$C$_6$H$_5$), 7.17 (d, $^4J_{HH}$=2.0 Hz, 1H, C3-H), 7.51 (d, $^4J_{HH}$=2.0 Hz, 1H, C5-H), 10.87 (s, 1H, OH).

2.3.3 [Lig6]H$_2$ (11) (Reaction of Compound (4) from Example 2.1.4)

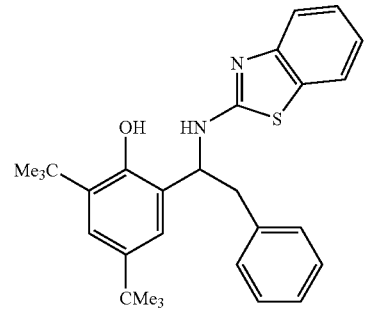

$^1$H-NMR (400 MHz, C$_6$D$_6$): δ=1.45 (s, 9H, 4-C(CH$_3$)$_3$), 1.70 (s, 9H, 6-C(CH$_3$)$_3$), 2.83 (d, $^3J_{HH}$=7.6 Hz, 2H, CH$_2$), 4.45 (d, $^3J_{HH}$=7.2 Hz, 1H, NH), 5.63 (quart, $^3J_{HH}$=7.6 Hz, 1H, CH), 6.77 (t, $^3J_{HH}$=7.6 Hz, 1H, benzothiazolyl-C6-H), 6.95 (m, 7H, benzothiazolyl-C5-H and -C7-H, CH$_2$C$_6$H$_5$), 7.22 (d, $^4J_{HH}$=2.4 Hz, 1H, C3-H), 7.52 (d, $^4J_{HH}$=2.4 Hz, 1H, C5-H), 7.58 (d, $^3J_{HH}$=8.0 Hz, 1H, benzothiazolyl-C4-H), 11.13 (s, 1H, OH).

3. Syntheses of Complexes 3.1 [Lig1]Ti(NMe$_2$)$_2$ (12) (Reaction of Compound (5) from Example 2.2.1)

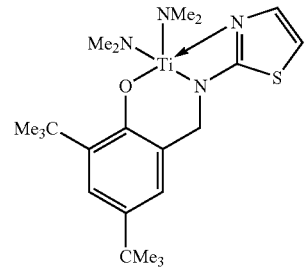

A solution of the ligand [Lig1]H$_2$ (5) (86 mg, 270 μmol) in 5 ml of toluene was added dropwise to the yellow solution of Ti(NMe$_2$)$_4$ (60 mg, 268 μmol) in 5 ml of toluene at room temperature while stirring. During this addition, the color of the reaction solution changed to dark red. After the addition was complete, the solution was stirred for another 1 hour. The volatile constituents of the reaction mixture were subsequently removed under reduced pressure, and the residue was taken up in pentane and stirred for 15 minutes. After removal of the solvent, the product was dried under reduced pressure. This gave [Lig1]Ti(NMe$_2$)$_2$ (12) in quantitative yield in the form of a reddish brown solid.

$^1$H-NMR (400 MHz, C$_6$D$_6$): δ=1.39 (s, 9H, C4-C(CH$_3$)$_3$), 1.72 (s, 9H, C6-C(CH$_3$)$_3$), 3.15 (s, 12H, N(CH$_3$)$_2$), 4.35 (s, 2H, CH$_2$), 5.79 (d, $^3$J$_{HH}$=4.0 Hz, 1H, NCH=CHS), 6.95 (d, $^3$J$_{HH}$=4.0 Hz, 1H, NCH=CHS), 7.04 (d, $^4$J$_{HH}$=2.4 Hz, 1H, C3-H), 7.53 (d, $^4$J$_{HH}$=2.4 Hz, 1H, C5-H).

3.2 [Lig2]TiCl(tert-BuCp) (14) (Reaction of Compound (6) from Example 2.2.2)

3.2.1 [Lig2]Li$_2$(Et$_2$O)$_2$ (13)

0.56 ml (1.38 mmol) of a 2.5 M BuLi solution in ether was added dropwise to a solution of the ligand [Lig2]H$_2$ (6) (230 mg, 692 μmol) while stirring at −70° C. After the addition was complete, the mixture was allowed to warm slowly to room temperature. The volatile constituents of the reaction solution were then removed under reduced pressure and the residue was taken up in pentane. Cooling to −70° C. gave [Lig2]Li$_2$(Et$_2$O)$_2$ (13) in the form of colorless crystals. Yield: 81% (275 mg, 558 μmol).

$^1$H-NMR (400 MHz, THF-d$_8$): δ=1.10 (t, Et$_2$O), 1.21 (s, 9H, C4-C(CH$_3$)$_3$), 1.30 (s, 9H, C6-C(CH$_3$)$_3$), 1.81 (s, 3H, CH$_3$), 3.38 (quart, Et$_2$O), 4.50 (br, 2H, CH$_2$), 5.44 (s, 1H, NC(CH$_3$)=CHS), 6.83 (d, $^4$J$_{HH}$=2.4 Hz, 1H, C3-H), 6.99 (d, $^4$J$_{HH}$=2.4 Hz, 1H, C5-H).

3.2.2 [Lig2]TiCl(tert-BuCp) (14)

The lithium salt (13) (89 mg, 181 μmol) and (tert-BuCp)TiCl$_3$ (50 mg, 181 μmol) were placed in a reaction vessel. While cooling in ice and stirring, 10 ml of precooled pentane were added. The reaction mixture was subsequently stirred at room temperature for 2 hours. The precipitated LiCl was filtered off and the solvent was then removed from the solution under reduced pressure. This gave 94 mg (176 μmol, 97%) of the product in the form of a dark red solid.

$^1$H-NMR (400 MHz, C$_6$D$_6$): δ=1.11 (s, 9H, CpC(CH$_3$)$_3$), 1.31 (s, 9H, C4-C(CH$_3$)$_3$), 1.64 (s, 9H, C6-C(CH$_3$)$_3$), 2.10 (s, 3H, CH$_3$), 4.10 (d, $^2$J$_{HH}$=16.0 Hz, 1H, CH$_2$), 4.60 (d, $^2$J$_{HH}$=16.0 Hz, 1H, CH$_2$), 5.43 (s, 1H, NC(CH$_3$)=CHS), 6.48 (m, 2H, Cp-H), 6.52 (m, 1H, Cp-H), 6.63 (m, 1H, Cp-H), 6.91 (d, $^4$J$_{HH}$=2.2 Hz, 1H, C3-H), 7.44 (d, $^4$J$_{HH}$=2.2 Hz, 1H, C5-H).

3.3 {[Lig1]H}$_2$TiCl$_2$ (15) (Reaction of Compound (5) from Example 2.2.1)

A solution of the ligand [Lig1]H$_2$ (5) (154 mg, 483 μmol) in 8 ml of Et$_2$O was added dropwise to the orange solution of Ti(NMe$_2$)$_2$Cl$_2$ (100 mg, 483 μmol) in 8 ml of Et$_2$O while stirring at −70° C., resulting in the color of the reaction solution changing to dark red. The reaction mixture was allowed to warm slowly to room temperature, and the volatile constituents of the mixture were removed under reduced pressure during this time. The dark red solid was washed with 5 ml of cold pentane and subsequently dried under reduced pressure.

Yield (from NMR): 217 mg (228 μmol, 94%).

$^1$H-NMR (400 MHz, C$_6$D$_6$): δ=1.27 (s, 9H, C4-C(CH$_3$)$_3$), 1.34 (s, 9H, C6-C(CH$_3$)$_3$), 1.68 (s, 9H, C4-C(CH$_3$)$_3$), 1.77 (s, 9H, C6-C(CH$_3$)$_3$), 4.27 (d, $^2$J$_{HH}$(spin system 1)=14.8 Hz, 1H; d, $^2$J$_{HH}$(spin system 2)=14.4 Hz, 1H, CH$_2$), 4.90 (d, $^2$J$_{HH}$(spin system 2)=14.4 Hz, 1H, CH$_2$), 5.59 (d, $^3$J$_{HH}$(spin system 3)=4.4 Hz, 1H, NCH=CHS), 5.82 (d, $^3$J$_{HH}$(spin system 4)=2.8 Hz, 1H, NCH=CHS), 5.90 (d, $^2$J$_{HH}$(spin system 1)=14.8 Hz, 1H, CH$_2$), 6.80 (d, $^3$J$_{HH}$(spin system 3)=4.4 Hz, 1H, NCH=CHS), 6.84 (d, $^3$J$_{HH}$(spin system 4)=2.8 Hz, 1H, NCH=CHS), 7.25, 7.38, 7.46 and 7.54 (4H, C3-H, C5-H).

3.4 [Lig2]TiCl$_2$ (16) (Reaction of Compound (6) from Example 2.2.2)

A solution of the ligand [Lig1]H$_2$ (6) (120 mg, 361 mmol) in 10 ml of THF was added dropwise to a solution of Ti(NMe$_2$)$_2$Cl$_2$ (75 mg, 362 μmol) in 10 ml of THF at room temperature while stirring. After the addition was complete, the reaction mixture was stirred for a further 30 minutes, after which the volatile constituents of the mixture were removed under reduced pressure. The dark red solid was washed with 5 ml of cold pentane and subsequently dried under reduced pressure. Yield (from NMR): 217 mg (228 mmol, 94%).

$^1$H-NMR (400 MHz, THF-d$_8$): δ=1.31 (s, 9H, C4-C(CH$_3$)$_3$), 1.50 (s, 9H, C6-C(CH$_3$)$_3$), 2.43 (s, 3H, CH$_3$), 2.46 (br, HN(CH$_3$)$_2$), 4.20 (br, HN(CH$_3$)$_2$), 4.65 (s, 2H, CH$_2$), 6.38 (s, 1H, NC(CH$_3$)=CHS), 7.23 (s, 1H, C3-H), 7.26 (s, 1H, C5-H).

3.5 [Lig3]Ti(Oi-Pr)$_2$ (17) (Reaction of Compound (7) from Example 2.2.3)

A solution of the ligand [Lig3]H$_2$ (7) (56 mg, 169 mmol) in 4 ml of Et$_2$O was added dropwise to a solution of 49 mg (169 μmol) of Ti(Oi-Pr)$_4$ in 4 ml of Et$_2$O at room temperature while stirring. After the addition was complete, the mixture was stirred for a further 2 hours. The volatile constituents of the reaction mixture were subsequently removed under reduced pressure. The residue was taken up in pentane and cooled to −70° C. After about 20 hours, 55 mg (111 μmol, 66%) of the complex (17) in the form of an orange solid were obtained.

$^1$H-NMR (400 MHz, C$_6$D$_6$): δ=0.82 (d, $^3$J$_{HH}$=6.0 Hz, 3H, OCH(CH$_3$)$_2$), 1.16 (d, $^3$J$_{HH}$=6.0 Hz, 3H, OCH(CH$_3$)$_2$), 1.20 (d, $^3$J$_{HH}$=6.0 Hz, 3H, OCH(CH$_3$)$_2$), 1.36 (s, 9H, C4-C(CH$_3$)$_3$), 1.70 (s, 9H, C6-C(CH$_3$)$_3$), 1.81 (s, 6H, CH$_3$), 4.38 (d, $^2$J$_{HH}$=14.6 Hz, 1H, CH$_2$), 4.80 (m, 1H, OCH(CH$_3$)$_2$), 5.07 (m, 1H, OCH(CH$_3$)$_2$), 5.32 (d, $^2$J$_{HH}$=14.6 Hz, 1H, CH$_2$), 7.35 (s, 2H, NCH=CHS, C3-H), 7.46 (d, $^4$J$_{HH}$=2.4 Hz, 1H, C5-H).

3.6 {[Lig3]H}$_2$Ti(Oi-Pr)$_2$ (18) (Reaction of Compound (7) from Example 2.2.3)

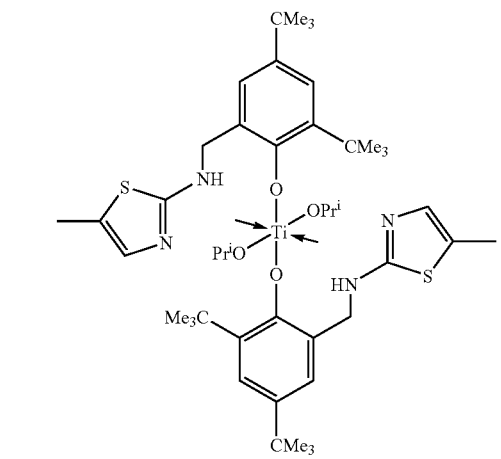

A solution of the ligand [Lig3]H$_2$ (7) (145 mg, 436 μmol) in 4 ml of Et$_2$O was added dropwise to a solution of 62 mg (218 μmol) of Ti(Oi-Pr)$_4$ in 4 ml of Et$_2$O at room temperature while stirring. After the addition was complete, the mixture was stirred for a further two hours. The volatile constituents of the reaction mixture were subsequently removed under reduced pressure. This gave the complex (18) in quantitative yield in the form of a yellow solid.

¹H-NMR (400 MHz, C₆D₆): δ=0.95 (d, ³J$_{HH}$=6.0 Hz, 12H, OCH(CH₃)₂), 1.41 (s, 18H, C4-C(CH₃)₃), 1.54 (s, 6H, CH₃), 1.80 (s, 18H, C6-C(CH₃)₃), 3.69 (d, ²J$_{HH}$=13.2 Hz, 2H, CH₂), 4.70 (sept, ³J$_{HH}$=6.0 Hz, 2H, OCH(CH₃)₂), 4.96 (d, 2J$_{HH}$=13.2 Hz, 2H, CH₂), 5.65 (s, 2H, NCH=CHS), 7.24 (d, ⁴J$_{HH}$=2.4 Hz, 2H, C3-H), 7.55 (d, ⁴J$_{HH}$=2.4 Hz, 2H, C5-H), 11.77 (s, 2H, NH).

3.7 [Lig5]Ti(Oi-Pr)₂ (19) (Reaction of Compound (9) from Example 2.3.1)

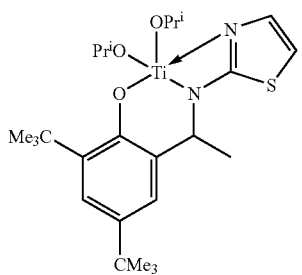

A solution of the ligand [Lig5]H₂ (9) (115 mg, 346 μmol) was added dropwise to a solution of Ti(Oi-Pr)₄ (130 mg, 457 μmol) in 15 ml of Et₂O at 0° C. while stirring. After the addition was complete, the reaction mixture was stirred for another 2 hours at room temperature, after which the volatile constituents of the mixture were removed under reduced pressure. The residue was taken up in pentane and cooled to –70° C. The precipitated orange solid was filtered off with cooling and dried under reduced pressure.

Yield: 71% (122 mg, 246 μmol).

¹H-NMR (400 MHz, C₆D₆): δ=0.81 (d, ³J$_{HH}$=6.4 Hz, 3H, OCH(CH₃)₂), 1.12 (d, ³J$_{HH}$=6.4 Hz, 3H, OCH(CH₃)₂), 1.20 (d, ³J$_{HH}$=6.0 Hz, 3H, OCH(CH₃)₂), 1.24 (d, ³J$_{HH}$=6.0 Hz, 3H, OCH(CH₃)₂), 1.33 (s, 9H, C4-C(CH₃)₃), 1.68 (s, 9H, C6-C(CH₃)₃), 1.83 (d, ³J$_{HH}$=6.8 Hz, 3H, CH(N)(CH₃)), 4.78 (sept, ³J$_{HH}$=6.4 Hz, 1H, OCH(CH₃)₂), 4.85 (quart, ³J$_{HH}$=6.8 Hz, 1H, CH(N)(CH₃)), 4.93 (sept, ³J$_{HH}$=6.0 Hz, 1H, OCH (CH₃)₂), 6.01 (d, ³J$_{HH}$=4.4 Hz, 1H, NCH=CHS), 7.22 (d, ⁴J$_{HH}$=2.4 Hz, 1H, C3-H), 7.43 (d, ⁴J$_{HH}$=2.4 Hz, 1H, C5-H), 7.79 (d, ³J$_{HH}$=4.4 Hz, 1H, NCH=CHS).

3.8 [Lig1]Hf(NMe₂)₂ (20) (Reaction of Compound (5) from Example 2.2.1)

A solution of the ligand [Lig1]H₂ (5) (41 mg, 129 μmol) in 8 ml of Et₂O was added dropwise to a solution of Hf(NMe₂)₄ (46 mg, 130 μmol) in 8 ml of Et₂O while stirring at –70° C. The reaction mixture was allowed to warm slowly to room temperature and the volatile constituents of the mixture were removed under reduced pressure. The residue was taken up in 5 ml of pentane, stirred at room temperature for 15 minutes and subsequently dried under reduced pressure. Yield (from NMR): 69 mg (118 μmol, 91%).

¹H-NMR (400 MHz, C₆D₆): δ=1.28 (s, 9H, C4-C(CH₃)₃), 1.33 (s, 9H, C6-C(CH₃)₃), 1.47 (s, 9H, C4-C(CH₃)₃), 1.71 (s, 9H, C6-C(CH₃)₃), 2.70 (s, 6H, N(CH₃)₂), 2.97 (s, 6H, N(CH₃)₂), 3.18 (s, 6H, N(CH₃)₂), 3.35 (s, 6H, N(CH₃)₂), 3.55 (d, ²J$_{HH}$(spin system 1)=14.0 Hz, 1H, CH₂), 3.86 (d, ²J$_{HH}$(spin system 1)=14.0 Hz, 1H, CH₂), 4.11 (d, ²J$_{HH}$(spin system 2)=15.8 Hz, 1H, CH₂), 5.03 (d, ²J$_{HH}$(spin system 2)=15.8 Hz, 1H, CH₂), 5.64 (d, ³J$_{HH}$(spin system 3)=4.0 Hz, 1H, NCH=CHS), 5.74 (d, ³J$_{HH}$(spin system 4)=4.4 Hz, 1H, NCH=CHS), 6.68 (d, ³J$_{HH}$(spin system 3)=4.0 Hz, 1H, NCH=CHS), 6.86 (s, 1H, C3-H), 7.25 (d, ³J$_{HH}$(spin system 4)=4.0 Hz, 1H, NCH=CHS), 7.33 (s, 1H, C3-H), 7.48 (s, 1H, C5-H), 7.49 (s, 1H, C5-H).

4. Polymerization of Ethene

The titanium complex, the toluene and MAO (methylaluminoxane) solution were placed in the reactor. Ethene was passed in while stirring. The pressure was kept constant during the reaction. At the end of the polymerization time, the reaction was stopped by venting the ethene pressure. The reaction mixture was poured into 10% strength HCl/methanol solution. The colorless solid which had precipitated and the product suspended in the solution during the reaction were stirred in the precipitation solution for 2 hours. The polymer was then filtered off, washed with methanol and hexane, dried at 60° C. in an oil pump vacuum for 2 hours and subsequently analyzed.

4.1 [Lig3]Ti(Oi-Pr)₂ (17)/MAO

Conditions:
  2 mg (4.0 μmol) of [Lig3]Ti(Oi-Pr)₂ (17)
  1.54 g (4.0 mmol) of 7% strength MAO solution 40 ml of toluene
  T=50° C., t=30 min, P$_{ethene}$=4 bar
  Yield/activity: 55 mg of 27.5 kg$_{PE}$/(h·mol$_{Ti}$)

4.2 [Lig3]Ti(Oi-Pr)₂ (17)/i-Bu₃Al/MAO

Conditions:
  2 mg (4.0 μmol) of [Lig3]Ti(Oi-Pr)₂ (17)
  39 mg (197 μmol) of i-Bu₃Al
  1.54 g (4.0 mmol) of 7% strength MAO solution 40 ml of toluene
  T=50° C., t=30 min, P$_{etene}$=4 bar
  Yield/activity: 64 mg of 32.0 kg$_{PE}$/(h·mol$_{Ti}$)

4.3 {[Lig3]H}₂Ti(Oi-Pr)₂ (18)/MAO

Conditions:
  5 mg (6.0 μmol) of {[Lig3]H}₂Ti(Oi-Pr)₂ (18)
  567 mg (2.1 mmol) of 10% strength MAO solution 40 ml of toluene
  T=50° C., t=30 min, P$_{ethene}$=4 bar
  Yield/activity: 79 mg of 26.3 kg$_{PE}$/(h·mol$_{Ti}$)

4.4 {[Lig1]H}₂TiCl₂ (15)/MAO

Conditions:
  5 mg (6.5 μmol) of {[Lig1]H}₂TiCl₂ (15)
  883 mg (2.29 mmol) of 7% strength MAO solution 40 ml of toluene
  T=25° C., t=30 min, p$_{ethene}$=4 bar
  Yield/activity: 237 mg of 72.9 kg$_{PE}$/(h·mol$_{Ti}$)

4.5 [Lig5]Ti(Oi-Pr)₂ (19)/MAO

Conditions:
  2 mg (4.0 μmol) of [Lig3]Ti(Oi-Pr)₂ (19)
  1.54 g (4.0 mmol) of 7% strength MAO solution 40 ml of toluene
  T=50° C., t=30 min P$_{ethene}$=4 bar
  Yield/activity: 136 mg of 68.0 kg$_{PE}$/(h·mol$_{Ti}$)

We claim:

1. A compound of the formula Ia or Ib

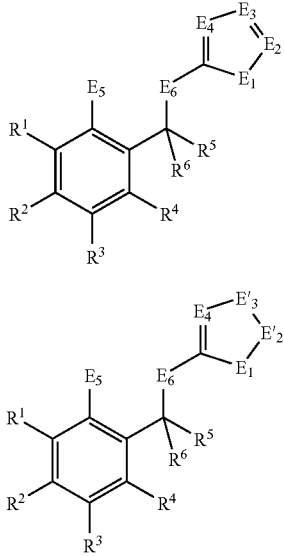

where,
in the formula Ia,
$E_1$ is O, S, Se, Te, NR, $CR_2$, or PR;
$E_2$, $E_3$ are each CR, N, P;
$E_4$ is N, or P;
$E_5$ is OH, SH, NHR, OR', SR', or NRR';
$E_6$ is NH, PH, NR', or PR';
$R^5$, $R^6$ are each hydrogen or a linear, branched or cyclic alkyl radical or an aryl radical;
$R^1$, $R^2$, $R^3$, $R^4$ are each hydrogen, a linear, branched or cyclic alkyl radical, an aryl radical, a halogen or a nitro group;
R is hydrogen, a linear, branched or cyclic alkyl radical;
R' is a linear, branched or cyclic alkyl radical;
where at least one of the groups $E_5$ and $E_6$ contains a hydrogen atom; and in the formula Ib,
the symbols $E_1$, $E_4$, $E_5$, $E_6$, $R^5$, $R^6$, $R^1$, $R^2$, $R^3$, $R^4$, R and R' are as defined in formula Ia;
and
$E'_2$ and $E'_3$ are each O, S, Se, Te, NR, $CR_2$, or PR.

2. A compound as claimed in claim 1, wherein $E_1$ is S.

3. A compound as claimed in claim 1, wherein $E_4$ is N.

4. A compound as claimed in claim 1, wherein $E_6$ is NH.

5. A process for preparing a compound as claimed in claim 1, which comprises reacting a compound of the formula IIa or IIb with a compound of the formula III to form a compound of the formula IVa or IVb (step a)) and subsequently reducing the compound of the formula IVa or IVb to give a compound of the formula Ia or Ib (step b)):

a) 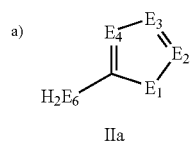 or 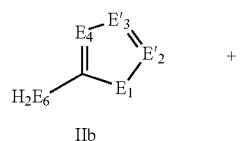 +

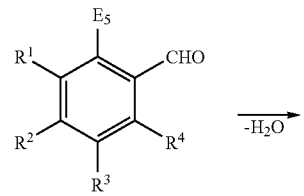

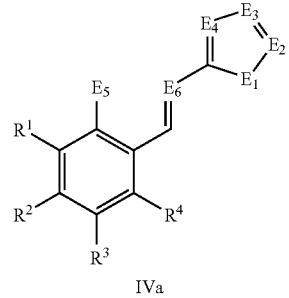

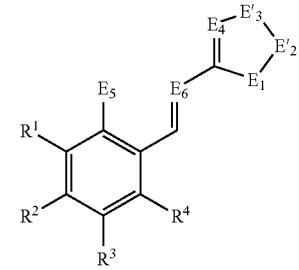

b) IVa or IVb $\xrightarrow{\text{Reduction}}$ Ia or Ib where
$E_1$ is O, S, Se, Te, NR, $CR_2$, or PR;
$E_2$, $E_3$ are each CR, N, or P;
$E'_2$, $E'_3$ are each O, S, Se, Te, NR, $CR_2$, or PR;
$E_4$ is N, or P;
$E_5$ is OH, SH, NHR, OR', SR', or NRR';
$E_6$ is NH, PH, NR', or PR';
$R^5$, $R^6$ are each hydrogen or a linear, branched or cyclic alkyl radical or an aryl radical;
$R^1$, $R^2$, $R^3$, $R^4$ are each hydrogen, a linear, branched or cyclic alkyl radical, an aryl radical, a halogen or a nitro group;
R is hydrogen, a linear, branched or cyclic alkyl radical; and
R' is a linear, branched or cyclic alkyl radical;
where at least one of the groups $E_5$ and $E_6$ contains a hydrogen atom.

6. A metal complex comprising a compound as claimed in claim 1.

7. A metal complex of the formula V $$L_xMR''_yY_z \qquad (V)$$

where
L is a monoanionic or dianionic ligand derived from a compound of the formula Ia or Ib as claimed in claim 1
where,
in the case of a dianionic ligand,
$E_5$ is $O^-$, $S^-$, or $RN^-$; and
$E_6$ is $N^-$or P, and, in the case of a monoanionic ligand,
either
$E_5$ is $O^-$, $S^-$, or $RN^-$ and
$E_6$ is NR or PR,
or
$E_5$ is OR, SR, or NRR' and
$E_6$ is N, or P;
and $E_1$ is O, S, Se, Te, NR, $CR_2$, or PR;
$E_2$, $E_3$ are each CR, N, or P;
$E'_2$, $E'_3$ are each O, S, Se, Te, NR, $CR_2$, or PR;
$E_4$ is N, or P;
$R^1$, $R^2$, $R^3$, $R^4$ are each hydrogen, a linear, branched or cyclic alkyl radical, an aryl radical, a halogen or a nitro group;
$R^5$, $R^6$ are each hydrogen or a linear, branched or cyclic alkyl radical or an aryl radical;
R is hydrogen, a linear, branched or cyclic alkyl radical; and
R' is a linear, branched or cyclic alkyl radical;
and, when L is a dianionic ligand,
M is Ti, Zr, Hf, V, Nb, Ta, Cr, Mo, or W;
R" is hydrogen, a hydrocarbon radical, $NR'''_2$, OR''', halogen, acetylacetonate, where R''' is hydrogen or a linear, branched or cyclic alkyl radical;
Y is a Lewis base;
x is 1 or 2;
y is from 1 to 4; and
z is from 0 to 2,
where R" and Y may be joined to form a joint radical and 2x+y corresponds to the valence of M;
or, when L is a monoanionic ligand,
M is Ti, Zr, Hf, V, Nb, Ta, Cr, Mo, W, Ni, Pd, Co, Fe, Cu, Ru, or Rh;
R" is hydrogen, a hydrocarbon radical, $NR'''_2$, OR''', halogen, or acetylacetonate, where R''' is hydrogen or a linear, branched or cyclic alkyl radical;
Y is a Lewis base;
x is 1, 2 or 3;
y is from 1 to 4; and
z is from 0 to 2;
where R" and Y may be joined to form a joint radical and x+y corresponds to the valence of M.

8. A metal complex as claimed in claim 7, wherein the ligand L is a dianionic ligand and M is Ti, Zr or Hf.

9. A metal complex as claimed in claim 8, wherein x is 1, y is 2 and z is 0.

10. A metal complex as claimed in claim 7, wherein the ligand L is a monoanionic ligand and M is Ti, Zr, Hf, Ni or Pd.

11. A metal complex as claimed in claim 10, wherein when M is Ti, Zr, or Hf, x is 2, y is 2 and z is 0 or x is 1, y is 3 and z is 0 and when M is Ni or Pd, x is 1, y is 1 and z is 0.

12. A process for preparing a metal complex as claimed in claim 7 by deprotonation of a compound of formula Ia or Ib by means of a base and subsequent reaction with a metal compound, or
by direct reaction of a compound of formula Ia or Ib with a metal compound,
where the metal compound comprises a metal M selected from the group consisting of Ti, Zr, Hf, V, Nb, Ta, Cr, Mo and W, when L is a dianionic ligand, or a metal M selected from the group consisting of Ti, Zr, Hf, V, Nb, Ta, Cr, Mo, W, Ni, Pd, Co, Fe, Cu, Ru and Rh, when L is a monoanionic ligand.

13. A catalytically active composition comprising:
a) a metal complex of the formula V as claimed in claim 7 as component A; and
b) at least one compound, as component B, selected from the group consisting of
(b1) an organometallic compound, as component B1,
(b2) an organoaluminum oxy compound, as component B2, and
(b3) a compound which reacts with the metal complex to form an ion pair, as component B3.

14. A catalytically active composition as claimed in claim 13 which further comprises a support material (component C) in addition to the components A and B.

15. A process for preparing a catalytically active composition as claimed in claim 13 which comprises bringing a metal complex of the formula V (component A) into contact with a compound (component B) selected from the group consisting of
(b1) an organometallic compound, as component B1,
(b2) an organoaluminum oxy compound, as component B2, and
(b3) a compound which reacts with the metal complex to form an ion pair, as component B3,
and optionally a support material (component C).

16. A process for the polymerization or copolymerization of olefins, which comprises polymerizing an olefin in the presence of a catalytically active composition as claimed in claim 13 or copolymerizing at least two different olefins in the presence of a catalytically active composition as claimed in claim 13.

* * * * *